US011000543B2

(12) United States Patent
Sun

(10) Patent No.: US 11,000,543 B2
(45) Date of Patent: *May 11, 2021

(54) SUBSTANCES CONTAINING AUCS AND PREPARATION METHOD AND USE THEREOF

(71) Applicant: Shenzhen Profound-View Pharma Tech Co., Ltd, Shenzhen (CN)

(72) Inventor: Taolei Sun, Wuhan (CN)

(73) Assignee: Shenzhen Profound-View Pharma Tech Co., Ltd, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/396,727

(22) Filed: Apr. 28, 2019

(65) Prior Publication Data

US 2019/0321396 A1 Oct. 24, 2019

Related U.S. Application Data

(60) Division of application No. 16/129,896, filed on Sep. 13, 2018, now abandoned, which is a continuation of
(Continued)

(51) Int. Cl.
*A61K 33/242* (2019.01)
*A61K 33/24* (2019.01)
(Continued)

(52) U.S. Cl.
CPC ............ *A61K 33/24* (2013.01); *A61K 9/5192* (2013.01); *A61K 47/542* (2017.08); *A61K 47/62* (2017.08); *A61K 47/64* (2017.08); *A61K 47/6923* (2017.08); *A61K 47/6929* (2017.08); *A61P 25/16* (2018.01); *A61P 25/28* (2018.01); *B22F 1/00* (2013.01); *C01G 7/003* (2013.01); *C12N 9/6472* (2013.01); *C22C 5/02* (2013.01); *A61K 9/167* (2013.01); *A61K 9/1682* (2013.01);
(Continued)

(58) Field of Classification Search
CPC .. A61K 33/242; A61K 33/24; A61K 47/6923; C01P 2004/64; B22B 1/0018; B22F 1/0022; B22F 1/0088; B22F 1/0096
See application file for complete search history.

(56) References Cited

U.S. PATENT DOCUMENTS

2016/0015742 A1* 1/2016 Yang .................. A61P 25/02
424/489

FOREIGN PATENT DOCUMENTS

JP A2000086684 A 3/2000

OTHER PUBLICATIONS

Hsieh et al. (Colloids and Surfaces B: Biointerfaces, 112, 2013, 525-529) (Year: 2013).*
(Continued)

*Primary Examiner* — Marcos L Sznaidman
*Assistant Examiner* — Rayna Rodriguez
(74) *Attorney, Agent, or Firm* — YIHE Intellectual Property Service Company

(57) ABSTRACT

Disclosed are a pharmaceutical use of a gold cluster and a substance containing the gold cluster and the preparation method and use thereof. The gold cluster and substance containing the gold cluster can inhibit the aggregation of Aβ and α-syn, has excellent effects on the levels of cell models and animal models, and can be used to prepare drugs for preventing and treating Alzheimer's disease and/or Parkinson's disease.

2 Claims, 21 Drawing Sheets

Related U.S. Application Data application No. PCT/CN2017/093671, filed on Jul. 20, 2017.

(51) Int. Cl.
| | |
|---|---|
| A61P 25/16 | (2006.01) |
| C22C 5/02 | (2006.01) |
| A61P 25/28 | (2006.01) |
| B22F 1/00 | (2006.01) |
| A61K 47/62 | (2017.01) |
| C01G 7/00 | (2006.01) |
| C12N 9/64 | (2006.01) |
| A61K 47/69 | (2017.01) |
| A61K 47/54 | (2017.01) |
| A61K 47/64 | (2017.01) |
| A61K 9/51 | (2006.01) |
| B22F 9/24 | (2006.01) |
| A61K 9/16 | (2006.01) |
| B82Y 5/00 | (2011.01) |

(52) U.S. Cl.
CPC .......... *B22F 1/0018* (2013.01); *B22F 1/0022* (2013.01); *B22F 1/0088* (2013.01); *B22F 1/0096* (2013.01); *B22F 9/24* (2013.01); *B22F 2999/00* (2013.01); *B82Y 5/00* (2013.01); *C01P 2004/64* (2013.01); *C01P 2004/90* (2013.01)

(56) References Cited

OTHER PUBLICATIONS

Gautier (Journal of the American Chemical Society, 128, 2006, 11079-11087) (Year: 2006).*

Gao et al (Angew. Chem. Int. Ed., 2015; 54:2245-2250, first published online Dec. 22, 2014) (Year: 2014).*

W. Yan, et al., Self-assembly of chiral nanoparticle pyramids with strong R/S optical activity, Journal of the American Chemical Society 2012, 134(36), Aug. 19, 2012, 15114-15121.

X. Yuan, et al., Balancing the rate of cluster growth and etching for gram-scale . . . Angewandte Chemie International Edition 2014, 53(18) Mar. 24, 2014, 4623-4627.

R. Liu, et al., Trehalose differentially inhibits aggregation and neurotoxicity of beta-amyloid 40 and 42, Neurobiology of Disease 2005, 20(1), Oct. 2005, 74-81.

C. V. Vorhees, et al., Morris water maze: procedures for assessing spatial and related forms of learning and memory, Nature Protocols 2006, 1, Jul. 27, 2016, 848-858.

V. N. Uversky, et al., Biophysical properties of the synucleins and their propensities to fibrillate: . . . Journal of Biological Chemistry 2002, 277(14), 2001103, 11970-11978.

D. S. Cassarino, et al., Elevated reactive oxygen species and antioxidant enzyme activities in animal . . . Biochimica et Biophysica Acta 1997, 1362(1), Nov. 28, 1997, 77-86.

G. A. Donnan, et al., Motor function in the 1-methyl-4-phenyl-1,2,3,6-tetrahydropyridine-treated mouse Journal of the Neurological Science 1987, 77(2-3), Feb. 1987, 185-191.

D. Luo, et al., N-Propargyl Caffeamide (PACA) Ameliorates Dopaminergic Neuronal Loss and Motor Dysfunctions . . . Molecular Neurobiology 2018, 55(3) Mar. 21, 2017 2258-2267.

Y. H. Liao, et al., Negatively charged gold nanoparticles inhibit Alzheimer's amyloid-βfibrillization, induce fibril dissociation, . . . Small 2012, 8(23), Aug. 23, 2012, 3631-3639.

Y. D. Alvarez, et al., Influence of gold nanoparticles on the kinetics of α-synuclein aggregation. Nano Letters 2013, 13(12), Nov. 12, 2013, 6156-6163.

S. Hsieh, et al., Gold nanoparticles as amyloid-like fibrillogenesis inhibitors, Colloids and Surfaces B: Biointerfaces, 2013, 112, Dec. 1, 2013, 525-529.

N. Gao, et al., Gold-nanoparticle-based multifunctional amyloid-β inhibitor against Alzheimer's disease. Chemistry—A European Journal 2015, 21(2), Nov. 5, 2014 829-835.

H. F. Qian, et al., Quantum sized gold nanoclusters with atomic precision, Accounts of Chemical Research 2012, 45(9), Jun. 21, 2012, 470-1479.

J. R. Wallbank, et al., Purine-stabilized green fluorescent gold nanoclusters for cell nuclei imaging applications, ACS Applied Materials . . . 2014, 6(3), Jan. 20, 2014, 2185-2191.

C. Gautier, et al., Chiral N-Isobutyryl-cysteine protected gold nanoparticles: preparation, . . . Journal of the American Chemical Society 2006, 128(34), Aug. 8, 2006, 11079-11087.

G. Li, et al., Atomically precise gold nanoclusters as new model catalysts, Accounts of Chemical Research 2013, 46(8), 1749-1758.

J. F. Parker, et al., The story of a monodisperse gold nanoparticle: Au25L18, Accounts of Chemical Research 2010, 43(9), 1289-1296.

S. H. Yau, et al., An ultrafast look at Au nanoclusters, Accounts of Chemical Research 2013, 46(7), Mar. 27, 2013, 1506-1516.

Gao G, et al. Chiral gold nanoclusters: A new near-infrared fluorescent probe. Acta Chim. Sinica 2016, 74, 363-368 (English Abstract).

Gong D, et al. Chiral Gold Nanoclusters: Synthesis, Properties and Applicaitons. Progress in Chemistry, 2016, 28(2/3): 296-307 (English Abstract).

Liao YH, et al. Negatively Charged Gold Nanoparticles Inhibit Alzheimer's Amyloid-beta Fibrillization, Induce Fibril Dissociation . . . Small 2012, 8:3631-3639.

Negishi Y, et al. Glutathione-Protected Gold Clusters Revisite: Bridging the Gap between Gold(I)-Thiolate Complexes and Thiolate . . . J. Am. Chem. Soc. 2005, 127:5261-5270.

Yang JA, et al. Study of Wild-Type a-Synuclein Binding and Orientation on Gold Nanoparticles. Langmuir 2013, 29, 4603-4615.

Antosova A, Anti-amyloidogenic activity of glutathione-covered gold nanoparticles. Materials Science and Engineering C 32 (2012) 2529-2535.

Haesuwannakij S. Size-controlled preparation of gold nanoclusters stabilized by high-viscosity hydrophilic polymers . . . Monatsh Chem (2014) 145:23-28.

Li L.Effect of polymer ligand structures on fluorescence of gold clusters prepared by photoreduction. Nanoscale, 2013, 5, 1986.

Toshio Sugaya Conference Lectures of the Physical Society of Japan, vol. 62, No. 1, Issue 2 (Japanese version).

Toshio Sugaya Conference Lectures of the Physical Society of Japan, vol. 62, No. 1, Issue 2 (English translation).

Zhang X. In vivo renal clearance, biodistribution, toxicity of gold nanoclusters. Biomaterials. 33 (2012) 4628-4638.

\* cited by examiner

SUBSTANCES CONTAINING AUCS AND PREPARATION METHOD AND USE THEREOF

FIELD OF THE INVENTION

The present invention relates to the technical field of nanometer nano-drugs, particularly to substances containing gold clusters (AuCs) and preparation method and application thereof.

BACKGROUND OF THE INVENTION

Neurodegenerative diseases are one of the major threats to human health. Their common pathological features are abnormal entanglement of proteins and their amyloidosis in nerve cells, and associated neuronal apoptosis and neurological impairment. Alzheimer's disease (AD) and Parkinson's disease (PD) are the most typical two of them. The clinical manifestations of AD are characterized by memory and cognitive dysfunction and changes in personality and behaviors, while the clinical manifestations of PD mainly include static tremor, bradykinesia, muscular rigidity, postural gait disorder and other dyskinesia. Both AD and PD mainly occur among old people, and the incidence increases with age. Taking AD for example, the incidence among the people above 65 is 5%, but above 30% among the people above 80. Therefore, the number of patients, suffering from these two diseases, is increasing incessantly as the prolonging of lifespans and the intensifying of population aging. AD, in particular, by far has affected more than 40 million patients, which would reach 150 million in 2050. For the United States alone, more than 200 billion U.S. dollars are spent on AD patients caring per year, as twice as cancer, which makes it the most expensive disease of the world. The number of PD patients of the world, according to a conservative estimation, has exceeded 10 million. However, the etiology of these two diseases is still unknown. In terms of clinical treatment, although several drugs have been approved by the US FDA to treat mild and moderate AD or PD, these drugs are neurotransmitter regulating drugs that can only temporarily improve the patient's cognitive or motor functions. The symptoms will rebound soon as soon as ceasing the drugs. Till now, no drug can terminate or reverse the pathological process of these two diseases. Therefore, it is extremely meaningful to develop new drugs for the treatment of AD or PD.

The research finds that: The amyloid proteins in the brains of AD patients are mainly β-amyloid (Aβ) protein and Tau protein, as well as a small amount of α-synuclein (α-syn), and the initial site of onset is the hippocampus that performs the functions of memory and learning and spatial orientation in the brain. The brain damage of PD patients starts from the substantia nigra, which is responsible for somatic motor function. The difference in the initial site of onset determines different symptoms of the patients with these two diseases. However, studies indicate that more than half of AD patients have dyskinesia in the later stage, and most PD patients also share the same symptoms of AD patients in the later stage. These phenomenons suggest that the two diseases have intrinsic correlations in pathogenesis and disease progression.

The formation of senile plaques in the brain is one of the basic pathological features of AD. As a main constituent substance in the senile plaques, Aβ is a polypeptide consisting of 36-43 amino acids, which is a hydrolysis product of amyloid precursor protein (APP), wherein the content of Aβ(1-40) accounts for more than 90% of the total amount of Aβ. The current study has clarified that although Aβ has normal physiological functions and can regulate acetylcholinergic signaling between synapses by regulating the catalytic activity of cholinesterase, but excessive aggregation and fibrosis of Aβ in the brain can cause synapse dysfunction, and subsequent secondary inflammatory response, leading to loss of neuronal function and neuron death Therefore, developing substances that can inhibit the aggregation and fibrosis of Aβ as well as block its neurotoxicity is one of the important approaches for the research and development of AD medication.

The pathological features of PD are mainly manifested as progressive loss of dopamine (DA)-ergic neurons in the nigrostriatal system, along with the production of Lewy bodies. The Lewy bodies mainly comprise hollow radial amyloid fibers formed by the aggregation of denatured α-syn. α-Syn is located at the presynaptic membrane terminal of neurons, and the natural state in the body is a soluble and unfolded state. Misfolding of α-Syn occurs under pathological conditions, generates β-sheet structures, which in turn are aggregated and fibrillated to form Lewy body lesions. Research indicates that amyloidosis of α-syn plays a key role in the pathological process of the disease. Therefore, inhibiting α-syn aggregation and fibrosis has become one of the approaches in the research and development of medication for PD's prevention and treatment. On the other hand, 1-methyl-4-phenyl-1,2,3,6-tetrahydropyridine (MPTP) is a neurotoxin. It is not toxic per se, but after it enters the brain, 1-methyl-4-phenylpyridine cation (MPP+) generated from its metabolism can destroy DA-ergic neurons in the substantia nigra. At the same time, MPP+ can also interfere with NADH dehydrogenase, an important substance in the respiratory chain of mitochondrial metabolism, then causes cell death and accumulation of free radicals. The mass death of DA-ergic neurons caused by this process severely affects the cerebral cortex's motion control, resulting in similar symptoms of PD. Therefore, MPTP and MPP+ are widely used in the establishment of PD-related animal models and cell models as well as the research and development of PD medications.

Gold nanoparticles are nanoscale gold particles (the diameter of the gold cores of the gold nanoparticles used in research is greater than 3 nm in general). Because of the unique optical and electric properties, good biocompatibility as well as convenient surface modification, gold nanoparticles are widely used in biology and related medical fields such as biosensors, medical imaging and tumor detection. Due to the chemical inertness and large specific surface area and the ability to penetrate the blood-brain barrier at low concentrations, gold nanoparticles are also used as drug carriers in the research of directional transport and controllable release of drugs, etc. In the recent years, research is made on binding gold nanoparticles with specific ligands (such as heteropolyacids and specific sequence polypeptides) that inhibit the aggregation of fibrotic proteins, achieving certain effects in vitro protein fibrosis inhibition experiments. (Y. H Liao, Y. J. Chang, Y. Yoshiike, Y. C. Chang, Y. R Chen, Small 2012, 8, 3631; Y. D. Alvarez, J. A Fauerbach, J. V. Pellegrotti, T. M. Jovin, E. A. Jares-Erijman, F. D. Stefani, Nano Letters 2013, 13, 6156; S. Hsieh, C. W. Chang, H. H. Chou, Colloids and Surfaces B: Biointerfaces, 2013, 112, 525), but the results of the cell model indicate that although there is a synergistic effect on cell viability when gold nanoparticles (gold core size is above 5 nm) are used together with compounds that have a protective effect on fibrin damaged cells (N. Gao, H. Sun, K. Dong, J. Ren, X. Qu, Chemistry-A European Journal 2015, 21, 829), the effect is not obvious when they are used alone. AD experiments at the level of animal model have not yet been reported. Moreover, in these researches, gold nanoparticles were mainly used as drug carriers other than as active ingredients.

Gold clusters (AuCs) are ultrafine gold nanoparticles with a gold core less than 3 nm in diameter. It contains only a few to hundreds of gold atoms, causing the face-centered cubic packing structure of the gold atoms in the conventional gold nanoparticles to collapse and the energy level to split, thus showing molecule-like properties that are completely different from the conventional gold nanoparticles of above 3 nm: On the one hand, due to energy level splitting, AuCs do not possess the surface plasmon effect and derived optical properties of conventional gold nanoparticles, but exhibit excellent fluorescence emission properties similar to semiconductor quantum dots. On the other hand, in the ultraviolet-visible absorption spectrum of AuCs, the plasmon resonance peak at 520±20 nm disappears, while one or more new absorption peaks appear above 560 nm, and such absorption peaks cannot be observed in conventional gold nanoparticles. Therefore, the disappearance of the plasmon resonance absorption peak (520±20 nm) and the appearance of the new absorption peaks above 560 nm in the UV-visible absorption spectrum are important indicators for judging whether AuCs are successfully prepared (H. F. Qian, M. Z. Zhu, Z. K. Wu, R. C. Jin, Accounts of Chemical Research 2012, 45, 1470). AuCs also have magnetic, electrical and catalytic properties and photothermal effects that are significantly different from those of conventional gold nanoparticles, so they have broad application prospects in the fields of single-molecule optoelectronics, molecular catalysis, and photothermal conversion.

In addition, AuCs have also been used in the fields of bioprobes and medical imaging due to their excellent fluorescence emission properties. For example, Sandeep Verma team uses purine-modified AuCs as green fluorescent probes for nucleus imaging, (J. It. Wallbank, D. Ghazaryan, A. Misra, Y. Cao, J. S. Th, B. A. Piot, M. Potemski, S. Wiedmann, U. Zeitler, T. L. M. Lane, S. V. Morozov, M. T. Greenaway, L. Evaes, A. K. Geim, V. I. Falko, K. S. Novoselov, A. Mishchenko, ACS Applied Materials & Interfaces 2014, 6, 2185). This type of literatures utilizes the fluorescence properties of AuCs and does not involve the medicinal activity of AuCs themselves.

SUMMARY OF THE INVENTION

The objective of the present invention is to tackle the technical defects in the prior art. In the first aspect, the present invention provides an AuCs-containing substance that has medicinal activity and comprises AuCs and ligand Y coating AuCs externally.

The gold core diameter of the AuCs is smaller than 3 nm, preferably 0.5-2.6 nm.

The ligand Y includes, but not limited to, one or more of L(D)-cysteine and its derivatives, cysteine-containing oligopeptides and their derivatives, and other thiol-containing compounds.

The L(D)-cysteine and its derivatives are preferably L(D)-cysteine, N-isobutyryl-L(D)-cysteine (L(D)-NIBC) or N-acetyl-L(D)-cysteine (L(D)-NAC).

The cysteine-containing oligopeptides and their derivatives are preferably cysteine-containing dipeptides, cysteine-containing tripeptides or cysteine-containing tetrapeptides.

The cysteine-containing dipeptides are preferably L-cysteine-L-arginine dipeptide (CR), L-arginine-L-cysteine dipeptide (RC), L-histidine-L-cysteine dipeptide (HC) or L-cysteine-L-histidine dipeptide (CH).

The cysteine-containing tripeptides are preferably glycine-L-cysteine-L-arginine tripeptide (GCR), L-proline-L-cysteine-L-arginine tripeptide (PCR), L-lysine-L-cysteine-L-proline tripeptide (KCP) or L-glutathione (GSH).

The cysteine-containing tetrapeptides are preferably glycine-L-serine-L-cysteine-L-arginine tetrapeptide (GSCR) or glycine-L-cysteine-L-serine-L-arginine tetrapeptide (GCSR).

Other thiol-containing compounds are preferably 1-[(2S)-2-methyl-3-thiol-1-oxopropyl]-L-proline, thioglycollic acid, mercaptoethanol, thiophenol, D-3-trolovol, N-(2-mercaptopropionyl)-glycine or dodecyl mercaptan.

The substance is powder or floc.

In the second aspect, the present invention provides a method for preparing the AuCs-containing substance, said method comprising the following steps:

(1) Dissolving $HAuCl_4$ in one of methanol, water, ethanol, n-propanol and ethyl acetate to get a solution A in which the concentration of $HAuCl_4$ is 0.01~0.03M;

(2) Dissolving ligand Y in a solvent to get a solution B in which the concentration of ligand Y is 0.01~0.18M;

(3) Mixing the solution A in step (1) with the solution B in step (2) at a mole ratio between $HAuCl_4$ and ligand Y 1:(0.01~100) (preferably 1:(0.1-10), more preferably 1:(1-10)), stirring them in an ice bath for 0.1~48 h (preferably 0.1-24 h, more preferably 0.5-2 h), adding 0.025~0.8M $NaBH_4$ solution (preferably water solution of $NaBH_4$, ethanol solution of $NaBH_4$ or methanol solution of $NaBH_4$), and then continuing to stir in an ice water bath for 0.1~12 h (preferably 0.1-2 h, more preferably 1-2 h), at a mole ratio between $NaBH_4$ and ligand Y 1: (0.01~100) (preferably 1:(0.1-8), more preferably 1:(1-8));

(4) Centrifuging the reaction solution in step (3) at 8000~17500 r/min for 10~100 min to obtain AuCs precipitate in different average particle sizes; preferably, using MWCO 3K~30K ultrafiltration tubes to centrifuge the reaction solution in step (3) at 8000~17500 r/min by gradient for 10~100 min to obtain AuCs in different average particle sizes;

(5) Dissolving the AuCs precipitate in different average particle sizes obtained in step (4) in water, putting it in a dialysis bag and dialyzing it in water at room temperature for 1~7 days;

(6) Freeze-drying the AuCs solution in the dialysis bag for 12~24 h to obtain the AuCs-containing substance.

The solvent in step (2) is one or more of methanol, ethyl acetate, water, ethanol, n-propanol, pentane, formic acid, acetic acid, diethyl ether, acetone, anisole, 1-propanol, 2-propanol, 1-butanol, 2-butanol, pentanol, ethanol, butyl acetate, tributyl methyl ether, isopropyl acetate, dimethyl sulfoxide, ethyl acetate, ethyl formate, isobutyl acetate, methyl acetate, 2-methyl1-propanol and propyl acetate.

In the third aspect, the present invention provides the application of the AuCs-containing substance in near-infrared fluorescent probes in the fields of catalyst preparation or molecular catalysis, chiral recognition, molecular detection, biomedical detection and imaging.

In the fourth aspect, the present invention provides the application of the AuCs-containing substance in the preparation of drugs for the disease associated with the aggregation and fibrosis of Aβ and for the disease associated with the aggregation and fibrosis of α-syn.

In the fifth aspect, the present invention provides the application of the AuCs-containing substance in the preparation of drugs for prevention and treatment of AD.

In the sixth aspect, the present invention provides the application of the AuCs-containing substance in the preparation of drugs for prevention and treatment of PD.

In the seventh aspect, the present invention provides the application of AuCs in the preparation of drugs for the disease associated with the aggregation and fibrosis of Aβ.

The disease associated with the aggregation and fibrosis of Aβ is AD.

The AuCs are modified with L-glutathione (GSH), N-acetyl-L(D)-cysteine (L(D)-NAC), N-isobutyryl-L(D)-cysteine (L(D)-NIBC), L-cysteine-L-arginine dipeptide (CR), L-arginine-L-cysteine dipeptide (RC), 1-[(2S)-2-methyl-3-thiol-1-oxopropyl]-L-proline (Cap) or L(D)-cysteine (L(D)-Cys).

In the eighth aspect, the present invention provides the application of AuCs in the preparation of medication for the disease associated with the α-syn aggregation and fibrosis.

The disease associated with the Aβ aggregation and fibrosis is PD.

The AuCs are modified with L-glutathione (GSH), N-acetyl-L(D)-cysteine (L(D)-NAC), N-isobutyryl-L(D)-cysteine (L(D)-NIBC), L-cysteine-L-arginine dipeptide (CR), L-arginine-L-cysteine dipeptide (RC), 1-[(2S)-2-methyl-3-thiol-1-oxopropyl]-L-proline (Cap) or L(D)-cysteine (L(D)-Cys).

The AuCs-containing substance provided by the present invention shows excellent effect on inhibiting Aβ and α-syn aggregation in the in vitro experiment for Aβ and α-syn aggregation inhibition, and shows excellent effect on improving cell viability in AD induced cell AD model and MPP$^+$ induced cell PD model experiments. In the transgenic mouse model of AD, the AuCs-containing substance can significantly improve the cognitive behavioral ability of sick mice, and plays a significant role in inhibiting the formation of Aβ (1-40) and Aβ (1-42) plaques in the hippocampus and cerebral cortex of mice. In the MPTP-induced PD mouse model, the AuCs-containing substance can significantly ameliorate and correct the dyskinetic disorder of MPTP lesion model mice, improve the motor abilities of sick mice, and substantially inhibit MPTP-induced specific apoptosis of DA-ergic neurons of substantia nigra and striatum of mice. And it also has good biosafety at the cell level and animal level. The above results indicate that the AuCs-containing substance provided by the present invention not only affects the aggregation and fibrosis of fibrotic proteins, but also influences the process of neurodegenerative diseases at deeper levels such as signaling functions related to energy metabolism and neurotransmitter metabolism of nerve cells. Therefore, the AuCs-containing substance provided by the present invention is important for the research and development of new medication for neurodegenerative diseases such as AD and/or PD.

On the other hand, since ligand molecules did not show any inhibitory effect in the kinetic experiment for in vitro inhibition of Aβ aggregation, and Aβ-lesioned AD cell model test, or any increase of cell viability in Aβ lesioned cell AD model and MPP$^+$-lesioned PD cell model, this suggests that the efficacy to AD and PD comes from AuCs other than ligands. Based on the medicinal activity of AuCs itself, development of competitive new medication is expected.

DETAILED DESCRIPTION OF THE EMBODIMENTS

Figure 1:
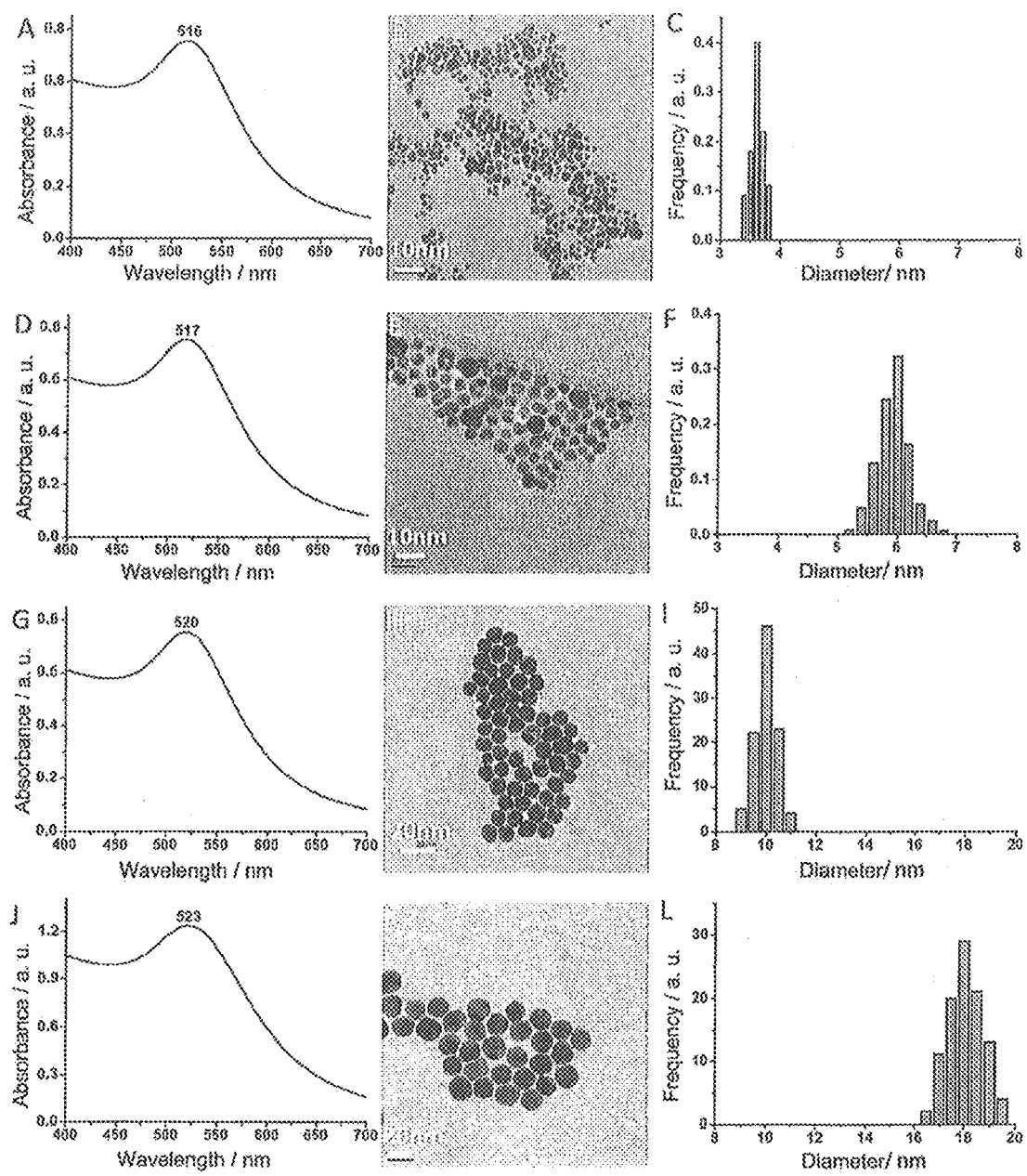
FIG. 1 shows ultraviolet-visible (UV) spectrums, transmission electron microscope (TEM) images and particle size distribution diagrams of ligand L-NIBC-modified gold nanoparticles with different particle sizes.

When studying the effect of gold nanoparticles with certain ligands on Aβ aggregation, the inventors found that when the gold core diameter of gold nanoparticles was changed from large to small, the promoting effect of gold nanoparticles modified with the same ligand on their surfaces on Aβ aggregation was converted into inhibitory one; when the particle size was small enough to become AuCs, complete inhibition of Aβ aggregation could be achieved. In addition, it was also found that AuCs also had a complete inhibitory effect on α-syn. In this effect, it is AuCs themselves other than ligands to play an inhibitory role.

Generally, the gold core diameter of the gold nanoparticles used in the research is greater than 3 nm, and when the diameter of the gold core is smaller than 3 nm, they are called AuCs. The disappearance of plasmon resonance absorption peak (520±20 nm) and the appearance of new absorption peaks above 560 nm in UV-visible absorption spectrum indicate that the AuCs are prepared successfully. Without ligands, AuCs cannot exist stably in a solution. It combines with thiol-containing ligand to form ligand-modified AuCs (or called AuCs) via Au—S bond.

The existing ligand-modified AuCs disclosed in the literature include AuCs modified with L-glutathione (GSH), N-acetyl-L(D)-cysteine (L(D)-NAC), N-isobutyryl-L(D)-cysteine (L(D)-NIBC), etc. The preparation process is shown in the literatures (H. F. Qian, M. Z. Zhu, Z. K. Wu, R C. Jin, Accounts of Chemical Research 2012, 45, 1470; C. Gautier, T. Bürgi, Journal of the American Chemical Society 2006, 128, 11079); they are mainly applied in the fields of catalysis, chiral recognition, molecular detection, biosensing, drug delivery and bioimaging (G. Li, R C. Jin, Accounts of Chemical Research 2013, 46, 1749; H. F. Qian, M. Z. Zhu, Z. K. Wu, R C. Jin, Accounts of Chemical Research 2012, 45, 1470; J. F. Parker, C. A. Fields-Zinna, R W. Murray, Accounts of Chemical Research 2010, 43, 1289; S. H. Yau, O. Varnavski, T. Goodson, Accounts of Chemical Research 2013, 46, 1506).

The present invention investigated the effects of AuCs on AD and/or PD, at least including: firstly, AuCs of different sizes containing different ligands (the ligands not having inhibitory effect on Aβ aggregation) were used as research objects. Through research at three levels of experiments, including in vitro experiments for inhibition of Aβ aggregation and -syn aggregation, Aβ induced AD cell model and MPP$^+$ induced PD cell model experiments, and AD transgenic mouse model and MPTP induced PD mouse model experiments, and in consideration of AuCs cytotoxicity, acute toxicity experiment in mice, in vivo distribution experiment in mice, etc., ligand-modified AuCs were provided, their application in the preparation of drugs treating AD and PD was found, and the results were compared with the experimental results of gold nanoparticles, indicating that gold nanoparticles with a diameter of greater than 3 nm do not have a desirable effect for this purpose, and cannot be used to prepare drugs treating AD or PD, while ligand-modified AuCs can be used to prepare drugs treating AD and/or PD.

Hereunder the present invention will be further detailed in embodiments, but those embodiments should not be understood as constituting any limitation to the present invention.

The purity of the raw materials used in the following embodiments shall be chemical purity or higher. They all may be purchased from the market.

Embodiment 1: Prepare Ligand-Modified AuCs

This embodiment discloses a method for preparing ligand-modified AuCs, said method comprising the following steps:

(1) Dissolving HAuCl$_4$ in one of methanol, water, ethanol, n-propanol and ethyl acetate to get a solution A in which the concentration of HAuCl$_4$ is 0.01~0.03M;

(2) Dissolving ligand Y in a solvent to get a solution B in which the concentration of ligand Y is 0.01~0.18M; ligand Y includes, but not limited to, L(D)-cysteine and other cysteine derivatives such as N-isobutyryl-L-cysteine (L-NIBC), N-isobutyryl-D-cysteine (D-NIBC), N-acetyl-L-cysteine and N-acetyl-D-cysteine, cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), L-glutathione (GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline, thioglycollic acid, mercaptoethanol, thiophenol, D-3-trolovol and dodecyl mercaptan; the solvent is one or more of methanol, ethyl acetate, water, ethanol, n-propanol, pentane, formic acid, acetic acid, diethyl ether, acetone, anisole, 1-propanol, 2-propanol, 1-butanol, 2-butanol, pentanol, ethanol, butyl acetate, tributyl methyl ether, isopropyl acetate, dimethyl sulfoxide, ethyl acetate, ethyl formate, isobutyl acetate, methyl acetate, 2-methy-1-propanol and propyl acetate;

(3) Mixing solution A and solution B so that the mole ratio between HAuCl$_4$ and ligand Y is 1:(0.01~100), stirring them in an ice bath for 0.1~48 h, adding 0.025~0.8M NaBH$_4$ water, ethanol or methanol solution, continuing to stir in an ice water bath and react for 0.1~12 h. The mole ratio between NaBH$_4$ and ligand Y is 1:(0.01~100);

(4) Using MWCO 3K~30K ultrafiltration tubes to centrifuge the reaction solution at 8000~17500 r/min by gradient for 10~100 min after the reaction ends to obtain ligand-modified AuCs precipitate in different average particle sizes (the specific gradient centrifugation is as described in (4) of Embodiment 2. The aperture of the filtration membranes for ultrafiltration tubes of different MWCOs directly decides the size of AuCs that can pass the membranes). This step may be omitted. In other words, after step (3) is completed, step (5) is started directly to obtain mixed AuCs in different sizes;

(5) Dissolving the AuCs precipitate in different average particle sizes obtained in step (4) in water, putting it in a dialysis bag and dialyzing it in water at room temperature for 1~7 days;

(6) Freeze-drying AuCs for 12~24 h after dialysis to obtain a powdery or flocculant substance, i.e., ligand-modified AuCs.

As detected (the specific detection method is shown in Embodiment 2), the particle size of the powdery or flocculant substance obtained by the foregoing method is smaller than 3 nm (distributed in 0.5-2.6 nm in general). The UV-visible absorption spectrum has one or more absorption peaks above 560 nm, and no obvious absorption peak at 520 nm. It is determined that the obtained powder or floc is AuCs.

Embodiment 2: Preparation and Confirmation of AuCs Modified with Different Ligands Taking ligand L-NIBC for example, the preparation and confirmation of AuCs modified with ligand L-NIBC are detailed.

(1) Weigh 1.00 g of $HAuCl_4$ and dissolve it in 100 mL of methanol to obtain a 0.03M solution A;

(2) Weigh 0.57 g of L-NIBC and dissolve it in 100 mL of glacial acetic acid (acetic acid) to obtain a 0.03M solution B;

(3) Measure 1 mL of solution A, mix it with 0.5 mL, 1 mL, 2 mL, 3 mL, 4 mL, 5 mL of solution B respectively (i.e. the mole ratio between $HAuCl_4$ and L-NIBC is 1:0.5, 1:1, 1:2, 1:3, 1:4, 1:5 respectively), react in an ice bath under stirring for 2 h, quickly add 1 mL of freshly prepared 0.03M (prepared by weighing 11.3 mg of $NaBH_4$ and dissolving it in 10 mL of ethanol) $NaBH_4$ water solution when the solution turns colorless from bright yellow, continue the reaction for 30 min after the solution turns dark brown, and add 10 mL of acetone to terminate the reaction.

(4) After the reaction, the reaction solution is subjected to gradient centrifugation to obtain L-NIBC modified AuCs powder with different particle sizes. Specific method: After the reaction is completed, the reaction solution is transferred to an ultrafiltration tube with MWCO of 30K and a volume of 50 mL, and centrifuged at 10000 r/min for 20 min, and the retentate in the inner tube is dissolved in ultrapure water to obtain powder with a particle size of about 2.6 nm. Then, the mixed solution in the outer tube is transferred to an ultrafiltration tube with a volume of 50 mL and MWCO of 10K, and centrifuged at 13,000 r/min for 30 min. The retentate in the inner tube is dissolved in ultrapure water to obtain powder with a particle size of about 1.8 nm. Then the mixed solution in the outer tube is transferred to an ultrafiltration tube with a volume of 50 mL and MWCO of 3K, and centrifuged at 17,500 r/min for 40 min. The retentate in the inner tube is dissolved in ultrapure water to obtain powder with a particle size of about 1.1 nm.

(5) Precipitate the powder in three different particle sizes obtained by gradient centrifugation, remove the solvent respectively, blow the crude product dry with $N_2$, dissolve it in 5 mL of ultrapure water, put it in a dialysis bag (MWCO is 3 KDa), put it in 2 L of ultrapure water, change water every other day, dialyze it for 7 days, freeze-dry it and keep it for future use.

Characterization experiment was conducted for the powder obtained above (ligand L-NIBC modified AuCs). Meanwhile, ligand L-NIBC modified gold nanoparticles are used as control. The method for preparing gold nanoparticles with ligand being L-NIBC refers to the reference (W. Yan, L. Xu, C. Xu, W. Ma, H. Kuang, L. Wang and N. A. Kotov, Journal of the American Chemical Society 2012, 134, 15114; X. Yuan, B. Zhang, Z. Luo, Q. Yao, D. T. Leong, N. Yan and J. Xie, Angewandte Chemie International Edition 2014, 53, 4623).

1. Observe the Morphology by Transmission Electron Microscope (TEM)

The test powders (L-NIBC modified AuCs sample prepared in Embodiment 2 and L-NIBC modified gold nanoparticle sample) was dissolved in ultrapure water to 2 mg/L as samples, and then test samples were prepared by hanging drop method. The specific method: 5 µL of the samples were dripped on an ultrathin carbon film, volatized naturally till the water drop disappeared, and then observe the morphology of the samples by JEM-2100F STEM/EDS field emission high-resolution TEM.

Figure 2:
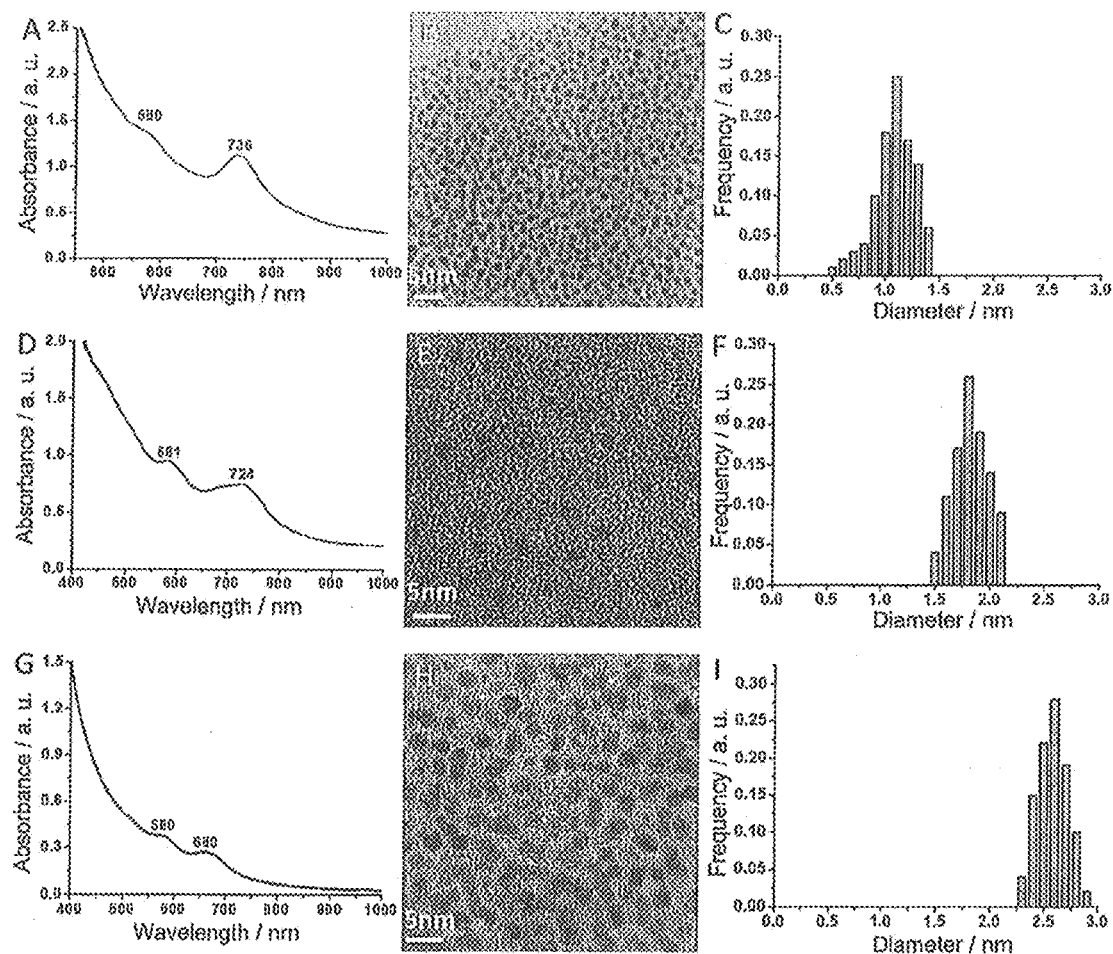
FIG. 2 shows ultraviolet visible spectrums, TEM images and particle size distribution diagrams of ligand L-NIBC-modified AuCs with different particle sizes.

The four TEM images of ligand L-NIBC modified gold nanoparticles are shown in panels B, E, H, and K of FIG. 1; the three TEM images of ligand L-NIBC modified AuCs are shown in panels B, E, and H of FIG. 2.

The images in FIG. 2 indicate that the L-NIBC-modified AuCs samples have a uniform particle size and good dispersibility, and the average diameter of L-NIBC-modified AuCs (refer to the diameter of gold core) is 1.1 nm, 1.8 nm and 2.6 nm respectively, in good accordance with the results in panels C, F and I of FIG. 2. In comparison, ligand L-NIBC modified gold nanoparticle samples have a larger particle size. Their average diameter (refer to the diameter of gold core) is 3.6 nm, 6.0 nm, 10.1 nm and 18.2 nm respectively, in good accordance with the results in panels C, F, I and L of FIG. 1.

2. Ultraviolet (UV)-Visible (Vis) Absorption Spectrum

The test powder was dissolved in ultrapure water till the concentration was 10 mg·$L^{-1}$, and was measured by UV-vis absorption spectrum at room temperature. The scanning range was 190-1100 nm, the sample cell was a standard quartz cuvette with an optical path of 1 cm, and the reference cell was filled with ultrapure water.

The UV-vis absorption spectra of the four ligand L-NIBC-modified gold nanoparticle samples with different sizes are shown in panels A, D, G and J of FIG. 1, and the statistical distribution of particle size is shown in panels C, F, I and L of FIG. 1; the UV-vis absorption spectra of three ligand L-NIBC modified AuCs samples with different sizes are shown in panels A, D and G of FIG. 2, and the statistical distribution of particle size is shown in panels C, F and I of FIG. 2.

FIG. 1 indicates that due to the surface plasmon effect, ligand L-NIBC modified gold nanoparticles had an absorption peak at about 520 nm. The position of the absorption peak is relevant with particle size. When the particle size is 3.6 nm, the UV absorption peak appears at 516 nm; when the particle size is 6.0 nm, the UV absorption peak appears at 517 nm; when the particle size is 10.1 nm, the UV absorption peak appears at 520 nm, and when the particle size is 18.2 nm, the absorption peak appears at 523 nm. None of the four samples has any absorption peak above 560 nm.

FIG. 2 indicates that in the UV absorption spectra of three ligand L-NIBC-modified AuCs samples with different particle sizes in Embodiment 2, the surface plasmon effect absorption peak at 520 nm disappeared, and two obvious absorption peaks appeared above 560 nm and the positions of the absorption peaks varied slightly with the particle sizes of AuCs. This is because AuCs exhibit molecule-like properties due to the collapse of the face-centered cubic structure, which leads to the discontinuity of the density of states of AuCs, the energy level splitting, the disappearance of plasmon resonance effect and the appearance of a new absorption peak in the long-wave direction. It could be concluded that the three powder samples in different particle sizes obtained in Embodiment 2 are all ligand-modified AuCs.

3. Fourier Transform Infrared Spectroscopy

Figure 3:
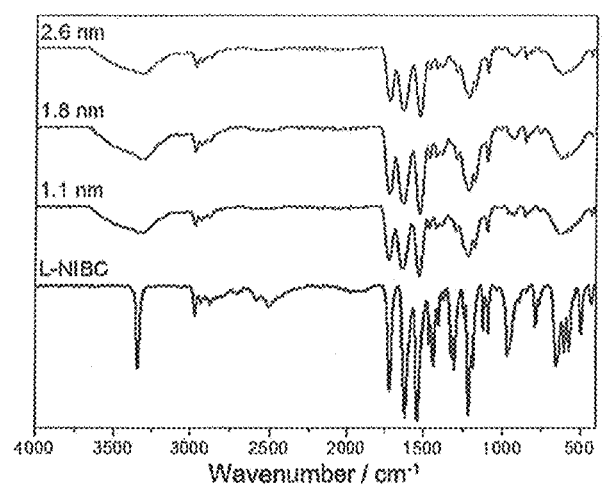
FIG. 3 shows infrared spectrums of ligand L-NIBC-modified AuCs with different particle sizes.

Infrared spectra were measured on a VERTEX80V Fourier transform infrared spectrometer manufactured by Bruker in a solid powder high vacuum total reflection mode. The scanning range is 4000-400 cm$^{-1}$ and the number of scans is 64. Taking the L-NIBC modified AuCs samples prepared in Embodiment 2 for example, the test samples were L-NIBC modified AuCs dry powder with three different particle sizes and the control sample was pure L-NIBC powder. The results are shown in FIG. 3.

surface of AuCs via Au—S bond. The figure also shows that the infrared spectrum of the ligand-modified AuCs is irrelevant with its size.

AuCs modified by other ligand Y were prepared by a method similar to the above method, except that the solvent of solution B, the feed ratio between HAuCl$_4$ and ligand Y, the reaction time and the amount of NaBH$_4$ added were slightly adjusted. For example: when L-cysteine, D-cysteine, N-isobutyryl-L-cysteine (L-NIBC) or N-isobutyryl-D-cysteine (D-NIBC) is used as ligand Y, acetic acid is selected as the solvent; when dipeptide CR, dipeptide RC or 1-[(2S)-2-methyl-3-thiol-1-oxopropyl]-L-proline is used as ligand Y, water is selected as the solvent, and so on and so forth; other steps are similar, so they won't be described in details here.

The present invention prepared and obtained a series of ligand-modified AuCs by the foregoing method. The ligands and the parameters of the preparation process are shown in Table 1.

TABLE 1

Preparation parameters of AuCs modified with different ligands in the present invention

| Embodiments | Ligand Y | Solvent used for solution B | Feed ratio between HAuCl$_4$ and Y | Time of reaction in an ice bath under stirring before addition of NaBH$_4$ | Mole ratio between HAuCl$_4$ and NaBH$_4$ | Time of reaction in an ice bath under stirring after addition of NaBH$_4$ |
|---|---|---|---|---|---|---|
| 1 | L-cysteine | Acetic acid | 1:3 | 2 h | 1:2 | 0.5 h |
| 2 | D-cysteine | Acetic acid | 1:3 | 2 h | 1:2 | 0.5 h |
| 3 | N-acetyl-L-cysteine | Ethanol | 1:4 | 1 h | 1:1 | 0.5 h |
| 4 | N-acetyl-D-cysteine | Ethanol | 1:4 | 1 h | 1:1 | 0.5 h |
| 5 | L-NIBC | Water | 1:4 | 0.5 h | 1:2 | 0.5 h |
| 6 | D-NIBC | Water | 1:4 | 0.5 h | 1:2 | 0.5 h |
| 7 | Other cysteine derivatives | Soluble solvent | 1:(0.1~100) | 0.5 h~24 h | 1:(0.1~100) | 0.1~24 h |
| 8 | CR | Water | 1:4 | 22 h | 2:1 | 0.5 h |
| 9 | RC | Water | 1:4 | 20 h | 2:1 | 0.5 h |
| 10 | HC | Water | 1:3 | 12 h | 1:2 | 2 h |
| 11 | CH | Ethanol | 1:4 | 16 h | 1:3 | 3 h |
| 12 | GSH | Water | 1:2 | 12 h | 1:1 | 3 h |
| 13 | KCP | Water | 1:3 | 15 h | 1:2 | 1 h |
| 14 | PCR | Water | 1:4 | 16 h | 1:3 | 2 h |
| 15 | GSCR | Water | 1:4 | 16 h | 1:3 | 1.5 h |
| 16 | GCSR | Water | 1:3 | 12 h | 1:2 | 2 h |
| 17 | Other oligopeptides containing cysteine | Soluble solvent | 1:(0.1~100) | 0.5 h~24 h | 1:(0.1~100) | 0.1~24 h |
| 18 | 1-[(2S)-2-methyl-3-thiol-1-oxopropyl]-L-proline | Water | 1:8 | 2 h | 1:7 | 1 h |
| 19 | Mercaptoethanol | Ethanol | 1:2 | 2 h | 1:1 | 1 h |
| 20 | Thioglycollic acid | Acetic acid | 1:2 | 2 h | 1:1 | 1 h |
| 21 | Thiophenol | Ethanol | 1:5 | 5 h | 1:1 | 1 h |
| 22 | D-3-trolovol | Water | 1:2 | 2 h | 1:1 | 1 h |
| 23 | N-(2-mercaptopropionyl)-glycine | Water | 1:2 | 2 h | 1:1 | 1 h |
| 24 | Dodecyl mercaptan | Methanol | 1:5 | 5 h | 1:1 | 1 h |
| 25 | Other compounds containing thiol | Soluble solvent | 1:(0.01~100) | 0.5 h~24 h | 1:(0.1~100) | 0.1~24 h |

FIG. 3 shows the infrared spectrum of L-NIBC modified AuCs with different particle sizes. Compared with pure L-NIBC (the curve at the top), the S-H stretching vibrations of L-NIBC modified AuCs with different particle sizes all disappeared completely at 2500-2600 cm$^{-1}$, while other characteristic peaks of L-NIBC were still observed, proving that L-NIBC molecules were successfully anchored to the The samples in embodiments listed in Table 1 are confirmed by the foregoing method. FIG. 7-FIG. 11 are UV spectra (panel A in FIG. 7-FIG. 11), infrared spectra (panel B in FIG. 7-FIG. 11), transmission electron microscope (TEM) images (panel C in FIG. 7-FIG. 11) and particle size distribution (panel D in FIG. 7-FIG. 11) of AuCs modified with ligand CR, RC, 1-[(2S)-2-methyl-3-thiol-1-oxopropyl]-L-proline (abbreviation: Cap), GSH and D-NIBC.

The results indicate that the diameters of AuCs modified with different ligands obtained from Table 1 are all smaller than 3 nm. Ultraviolet spectra also show disappearance of peak at 520±20 nm, and appearance of absorption peak above 560 nm. Only the position of this absorption peak varies slightly with ligand and particle size. Meanwhile, Fourier transform infrared spectrum also shows disappearance of ligand thiol infrared absorption peak (between the dotted lines in panel B of FIG. 7-FIG. 11), while other infrared characteristic peaks are all retained, suggesting that all ligand molecules have been successfully anchored to the surface of AuCs, and the present invention has successfully obtained AuCs modified with the ligands listed in Table 1.

Embodiment 3: In Vitro Aβ Aggregation Kinetic Experiment

This embodiment validated the functions of ligand-modified AuCs by in vitro experiment of Aβ aggregation kinetics, and compared the effects on Aβ aggregation kinetics with ligand-modified gold nanoparticles and independent use of ligand molecules to prove that the function is from AuCs other than ligand. The experiment used ThT fluorescent labeling method to characterize the kinetics of Aβ(1-40) aggregation and fibrosis.

Thioflavin T (abbreviation: ThT) is a dye specifically for dyeing amyloid fibers. When it is incubated together with monomers of polypeptides or proteins, its fluorescence does not change substantially. When it encounters amyloid polypeptides or proteins with a fiber structure, it will immediately couple with the amyloid polypeptides or proteins and its fluorescence intensity will increase exponentially. Just because of this property, ThT is widely used as a marker to monitor amyloidosis of peptides or proteins. The fibrosis process of Aβ(1-40) is also a nucleation-controlled polymerization process. Therefore, the growth curve of Aβ(1-40) fiber measured by ThT fluorescent labeling method is mainly divided into three stages: Initial stage, growth stage and platform stage. The initial stage is mainly a stage when Aβ(1-40) undergoes conformational transition to form misfolding and then aggregates and nucleates. The growth stage is a stage when Aβ(1-40) monomers are accumulated onto the cores of oligomers along the axial direction to form fibers and grow rapidly. The platform stage is a stage when all Aβ(1-40) molecules form mature long fibers, i.e., a stage when the fibers no longer grow. ThT fluorescent labeling method can conveniently monitor the kinetics process of fibrotic aggregation of Aβ(1-40) molecules.

1) Pretreatment of Aβ(1-40) Monomers

Freeze-dried powder of amyloid polypeptide Aβ(1-40) (Invitrogen Corp.) was dissolved in hexafluoroisopropanol (HFIP) to obtain a 1 g/L Aβ(1-40) solution, and the solution was inculated at room temperature for 2-4 h after sealing, then blowed to dry HFIP (for about 1 h) with high-purity nitrogen (N2, 99.9%) at an appropriate flow rate in a fume hood. Lastly the dried Aβ(1-40) was dissolved in 200 μL of DMSO, and after sealing, the solution was kept in a refrigerator at −20° C. for no more than one week for future use. Before use, the DMSO solution of the amyloid polypeptide was diluted with profuse phosphate buffer solution (PBS, 10 mM, pH=7.4) till the concentration of Aβ(1-40) reached 20 μM to obtain an Aβ(1-40) PBS solution. All the Aβ(1-40) PBS solutions for the experiments were prepared freshly.

2) Sample Preparation and Detection

Ligand-modified AuCs and gold nanoparticles were added to 20 μM Aβ(1-40) PBS respectively to form samples of AuCs modified with different ligands at different concentrations and different particle sizes, and samples of gold nanoparticles modified with different ligands correspondingly. The samples were incubated continuously in a 96-well plate at 37° C. by ThT fluorescent labeling method, and monitored the fluorescence intensity by microplate reader once every 10 minutes. The kinetic process of Aβ(1-40) aggregation was characterized through the change of fluorescence intensity of ThT.

Three sizes of L-NIBC-modified AuCs with particle sizes of 2.6 nm, 1.8 nm and 1.1 nm respectively prepared in Embodiment 2 were used as experiment groups. Four sizes of L-NIBC-modified gold nanoparticles with particle sizes of 18.2 nm, 10.1 nm, 6.0 nm and 3.6 nm respectively, and L-NIBC molecules uncombined with AuCs or gold nanoparticles were used as control groups. Every size of AuCs or gold nanoparticles were in six concentrations respectively, which were: 0 ppm (not containing AuCs, gold nanoparticles or L-NIBC, as blank control), 0.1 ppm, 1.0 ppm, 5.0 ppm, 10.0 ppm and 20.0 ppm respectively. L-NIBC molecules in two concentrations were used, which were: 1.0 ppm and 10.0 ppm respectively.

Figure 4:
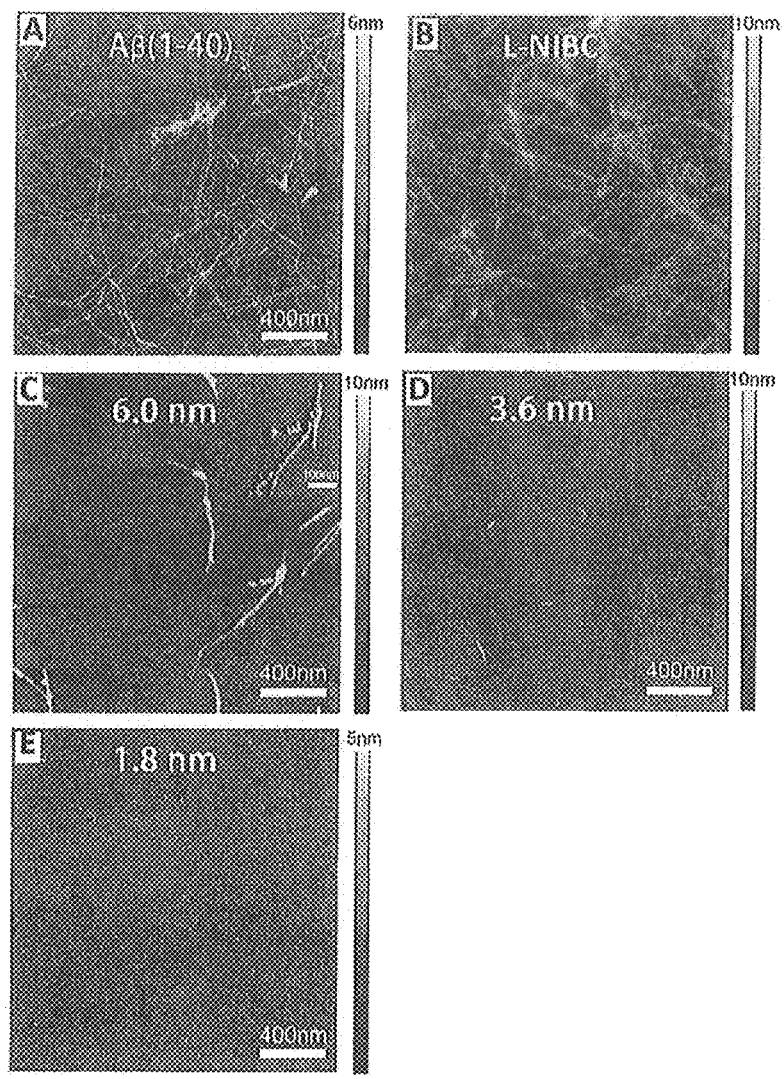
FIG. 4 shows AFM topographies after Aβ (1-40) and ligand L-NIBC-modified gold nanoparticles or AuCs are jointly incubated for 48 h.
Figure 5:
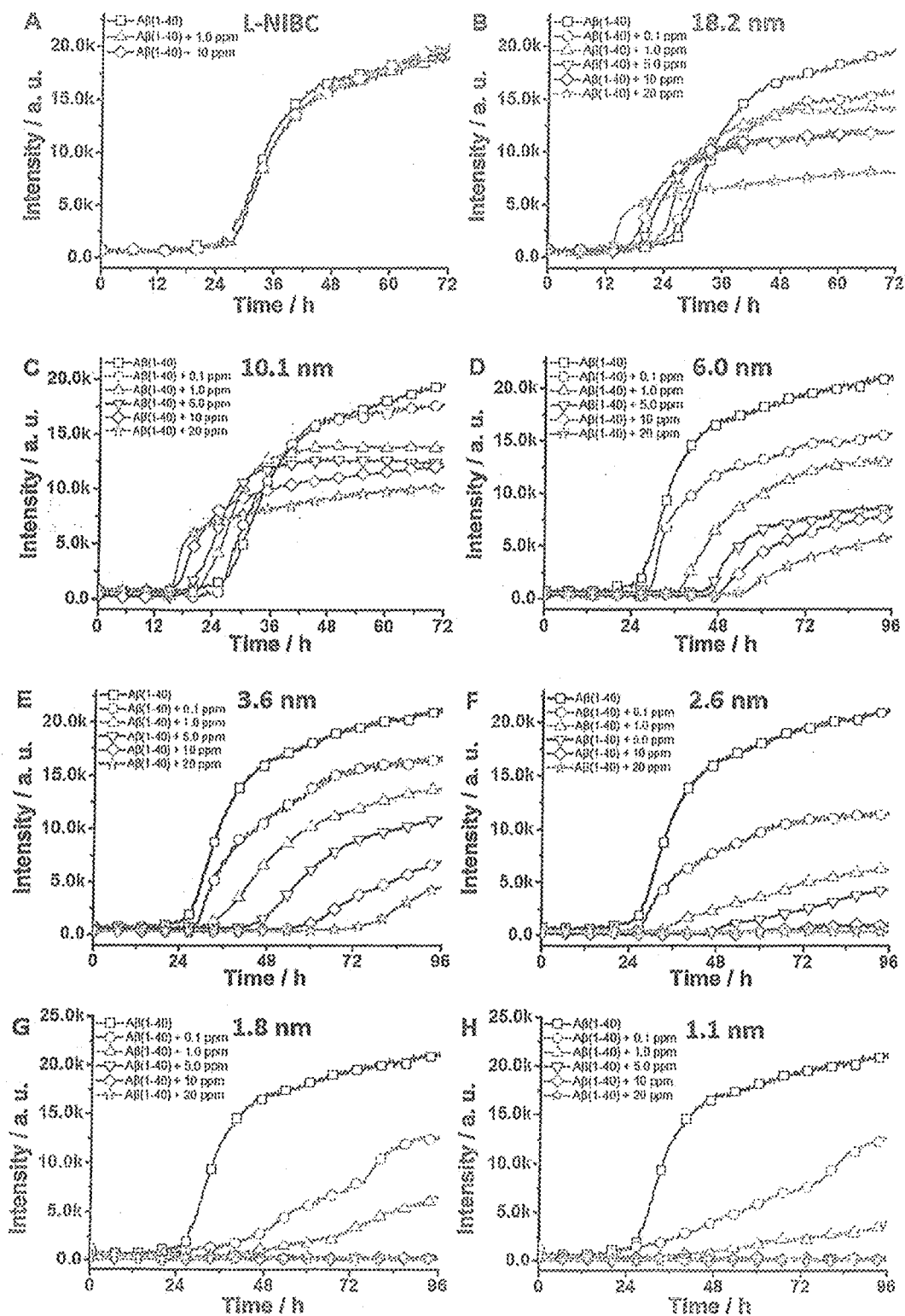
FIG. 5 shows kinetic curves of Aβ fibrosis of ligand L-NIBC-modified gold nanoparticles and AuCs of different particle sizes and different concentrations.

The results are shown in FIG. 4 and FIG. 5.

FIG. 4 shows AFM topographies of Aβ(1-40) after coincubating with each experiment group and control group for 48 h. Panel A is the AFM topography after Aβ(1-40) was incubated alone for 48 h. Panel B is an AFM topography after Aβ(1-40) was coincubated with L-NIBC for 48 h. Panel C and panel D are AFM topographies after Aβ(1-40) was coincubated with gold nanoparticles with an average particle size of 6.0 nm and 3.6 nm respectively (modified with L-NIBC) for 48 h. And panel B is an AFM topography after Aβ(1-40) was coincubated with AuCs in an average particle size of 1.8 nm (modified with L-NIBC) for 48 h.

In FIG. 5, the amyloidosis kinetics curve of Aβ(1-40) in different concentrations of L-NIBC is shown in panel A. The amyloidosis kinetics curves of Aβ(1-40) in different concentrations of gold nanoparticles with sizes of 18.2 nm, 10.1 nm, 6.0 nm and 3.6 nm respectively are shown in panel B-E. The amyloidosis kinetics curves of Aβ(1-40) in different concentrations of AuCs with sizes of 2.6 nm, 1.8 nm and 1.1 nm respectively are shown in panel F-H. The amyloidosis kinetics curves of Aβ in panels A-H are curves when Aβ(1-40) was coincubated gold nanoparticles or AuCs in different concentrations, □ represented 0 ppm (i.e., no gold nanoparticles and AuCs), ○ represented 0.1 ppm, Δ represented 1 ppm, represented 5 ppm, represented 10 ppm, ★ represented 20 ppm.

It could be seen from FIG. 4 that as control, Aβ fibers was filled in panel A; the same as panel B; though fibers reduced to some extent, long fibers could still be seen in panel C; though there was no long fibers, many Aβ short fibers still existed in panel D. It was indicated that L-NIBC had no obvious effect on the formation of Aβ(1-40) fibers. The addition of L-NIBC-modified small-size gold nanoparticles could delay the amyloidosis process of Aβ(1-40), but not inhibit completely because short fibers would continue to grow into long fibers after more time. It has neither long fibers nor short fibers in panel E of FIG. 4, what was suggested that L-NIBC-modified AuCs could inhibit the amyloidosis process of Aβ(1-40) completely.

FIG. 4 is a qualitative experiment, but FIG. 5 is a quantitative experiment. The result of FIG. 5 indicates that the addition of L-NIBC had no obvious effect on Aβ(1-40) amyloidosis kinetics (panel A of FIG. 5); for gold nanoparticles, when the particle diameter was greater than or equal to 10.1 nm, the addition of L-NIBC-modified gold nanoparticles pushed forward both the growth stage and platform stage of Aβ aggregation kinetics (when the concentration of gold nanoparticles was 20 ppm, the growth stage of Aβ aggregation kinetics was pushed forward to $12^{th}$ h, and the platform stage was pushed forward to $16^{th}$), suggesting that L-NIBC-modified gold nanoparticles could accelerate Aβ aggregation (panels B and C of FIG. 5); when the diameter of gold nanoparticles was smaller than or equal to 6.0 nm (panel D and E of FIG. 5), the starting time of Aβ aggregation could be delayed (when the concentration of L-NIBC-modified gold nanoparticles was 20 ppm, the growth stage of Aβ aggregation kinetics was delayed to $54^{th}$), suggesting that gold nanoparticles had an inhibitory effect on Aβ aggregation. However, FIG. 5 indicates that even if the concentration was very high (20.0 ppm), the addition of L-NIBC-modified gold nanoparticles was unable to inhibit completely (i.e., no growth stage appeared, and the fluorescent curve was completely flat). On the other hand, after addition of L-NIBC-modified gold nanoparticles, since the fluorescence emission peak of ThT locates at 515 nm, while the plasmon resonance absorption peak of L-NIBC-modified gold nanoparticles locates near 520 nm, the decrease of ThT fluorescent intensity observed here should be the partial quenching of the plasmon resonance effect of the gold nanoparticles to ThT fluorescence, but should not be attributed to the inhibitory effect of L-NIBC-modified gold nanoparticles on Aβ(1-40) aggregation.

Panels F-H of FIG. 5 indicate that all the L-NIBC-modified AuCs could significantly inhibit Aβ aggregation (the starting time of the growth stage was postponed. When the concentration of L-NIBC-modified AuCs was 5 ppm, the starting time of the growth stage in aggregation kinetics of 20 μM Aβ could be delayed to later than 50 h). When the concentration of L-NIBC-modified AuCs was 10 ppm or above, Aβ aggregation could be completely inhibited (growth stage did not appear, and the fluorescent curve was completely flat). The minimum concentration of L-NIBC-modified AuCs needed for complete inhibition is relevant to the ligand type and the diameter of AuCs. The minimum concentrations of L-NIBC-modified AuCs with sizes of 1.1 nm, 1.8 nm and 2.6 nm were 5.0 ppm, 5.0 ppm and 10.0 ppm respectively. Besides, as L-NIBC-modified AuCs do not have plasmon resonance effect, they do not have quenching effect on ThT fluorescence. Therefore, the decrease in fluorescence intensity observed here was entirely due to the inhibitory effect of L-NIBC-modified AuCs on Aβ(1-40) aggregation. The quantitative results of FIG. 5 are in good agreement with the qualitative results of FIG. 4.

This experiment indicates that: when the size of L-NIBC-modified gold nanoparticles is smaller than or equal to 6.0 nm, they have certain inhibitory effect on Aβ aggregation and fibrosis, but limitedly; L-NIBC-modified AuCs has the function of completely inhibiting Aβ aggregation and fibrosis. As L-NIBC molecules per se cannot influence the aggregation and fibrosis of Aβ (in view of panel B of FIG. 4 and panel A of FIG. 5), this function is from AuCs, but not L-NIBC ligand. This lays a foundation for the formation of medications for Aβ aggregation and fibrosis-related diseases, which can be classified as AuCs-containing substances as defined by the present invention.

Figure 12:
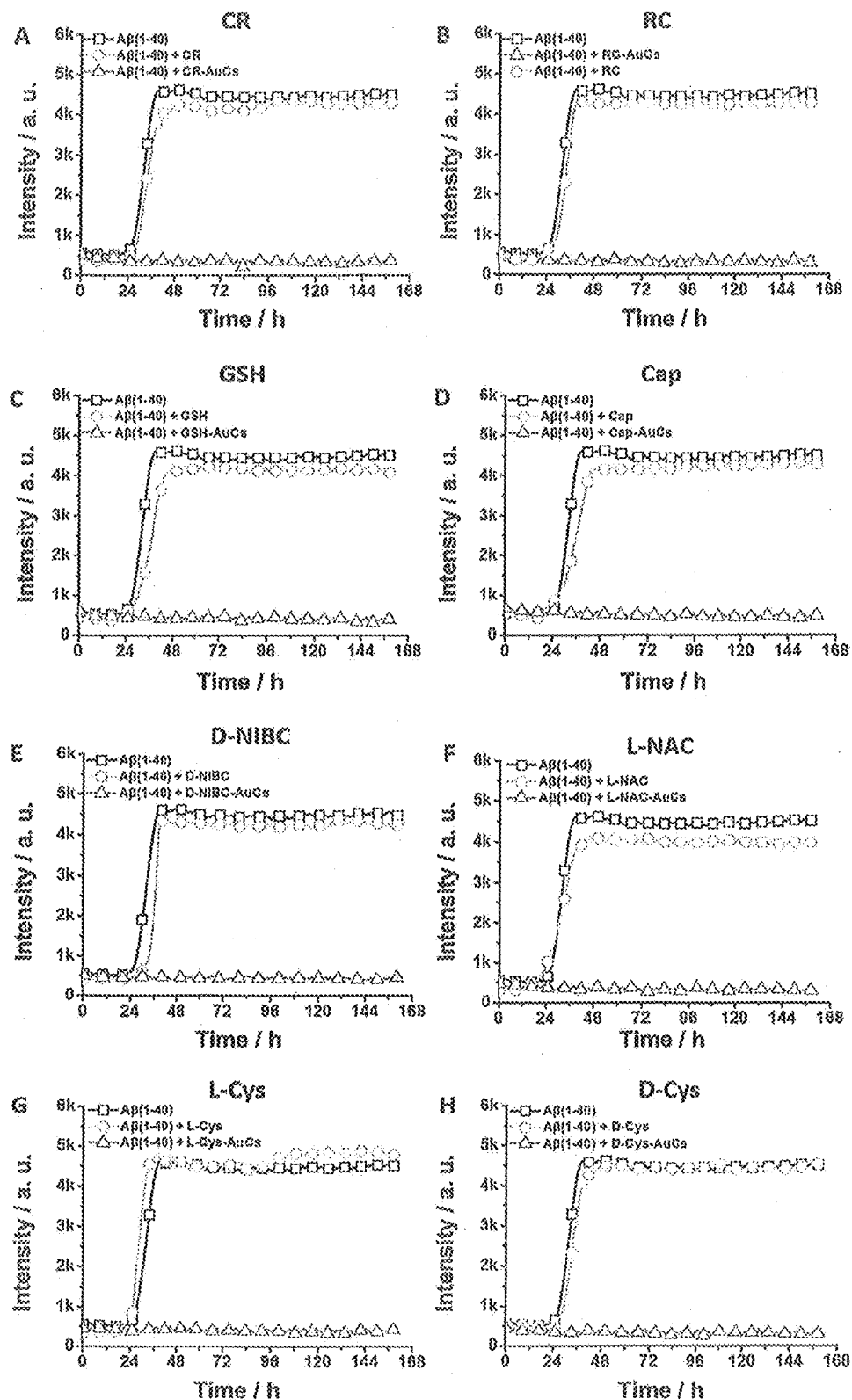
FIG. 12 shows curves of the inhibitory effect of AuCs modified with different ligands on the aggregation and fibrosis of Aβ (1-40).

This embodiment also validates the functions of AuCs modified with other ligands listed in Table 1. For example, panels A-H of FIG. 12 show the inhibitory effect of AuCs modified with CR, N-acetyl-L-cysteine (L-NAC), GSH, 1-[(2S)-2-methyl-3-thiol-1-oxopropyl]-L-proline (Cap), D-NIBC, RC or L-cysteine and D-cysteine (the dose is 10 ppm) on Aβ(1-40) aggregation and fibrosis. A similar phenomenon was observed for AuCs modified with different ligands, and the same conclusion can be made: These ligands per se cannot influence Aβ aggregation and fibrosis, the ligand-modified gold nanoparticles with a size of greater than 3 nm have a limited inhibitory effect on Aβ aggregation and fibrosis, and larger gold nanoparticles even promote Aβ aggregation and fibrosis; but ligand-modified AuCs have excellent inhibitory effect on Aβ aggregation and fibrosis, and when the concentration is above 5-10 ppm, effect of complete inhibition can be achieved, while the minimum concentration needed for complete inhibition varies slightly with ligand and particle size of AuCs. Likewise, these ligand-modified AuCs are classified into AuCs-containing substances defined in the present invention.

Embodiment 4: Experiment of Aβ Induced AD Cell Model

The cell viability was used as an index in the experiment of this embodiment. The test result of CCK-8 method reflected the effects of ligand-modified AuCs or gold nanoparticle samples on the toxicity of Aβ(1-40), and showed if ligand-modified AuCs or gold nanoparticles had a neuroprotective effect on the pathogenesis of amyloid protein misfolding. The cells used in the experiment were SH-SY5Y neuroblastoma cell line. Aβ-induced AD cell model was established according to the description in the literature (R. Liu, H. Barkhordarian, S. Emadi, C. B. Park, M. R Sierks, Neurobiology of Disease 2005, 20, 74). Specific method:

1) SH-sy5y cells (cells had passed to the sixth generation) in logarithmic growth phase were diluted with complete medium (MEM+10% FBS+1% penicillin–streptomycin) to get a cell suspension in a density of $5 \times 10^4$/mL. The suspension was inoculated 200 μL per well into a 96-well plate, and cultivated in an incubator with 5% $CO_2$ at 37° C. A sample was added when the cells attached to the wells.

2) 100 μL ligand-modified AuCs samples or ligand-modified gold nanoparticles samples, at different particle sizes and at concentrations of 0.04 ppm, 0.4 ppm, 4 ppm, 20 ppm, 40 ppm and 80 ppm respectively, which were dissolved by maintenance medium (MEM+2% FBS+1% penicillin-streptomycin) were added into the incubated suspension obtained from Step 1). After incubating in the incubator for 2 h, 100 μL 80 μM Aβ(1-40) was added, and then the mixture was incubated in the incubator for 24 h. In this way, the final concentrations of ligand-modified AuCs or ligand-modified gold nanoparticles were 0.01 ppm, 0.1 ppm, 1 ppm, 5 ppm, 10 ppm and 20 ppm respectively, while the final concentration of Aβ(1-40) was 20 μM. Meanwhile, there were groups below: the blank control group did not contain SH-sy5y cells, the negative control group contained SH-sy5y cells but did not contain ligand-modified AuCs or ligand-modified gold nanoparticles and Aβ(1-40), the cell model control group contained SH-sy5y cells and Aβ(1-40) (final concentration was 20 μM) only, and the ligand control group contained SH-sy5y cells, Aβ(1-40) (final concentration was 20 μM) and L-NIBC (final concentration was 20 ppm). The culture medium was removed, maintenance medium (MEM) containing 10% CCK-8 at 100 μL/well was added and was incubated for 4 h, the absorbance of each well at 450 nm was measured to reflect the prevention and treatment effects of ligand-modified AuCs on Aβ(1-40) lesion.

Figure 6:
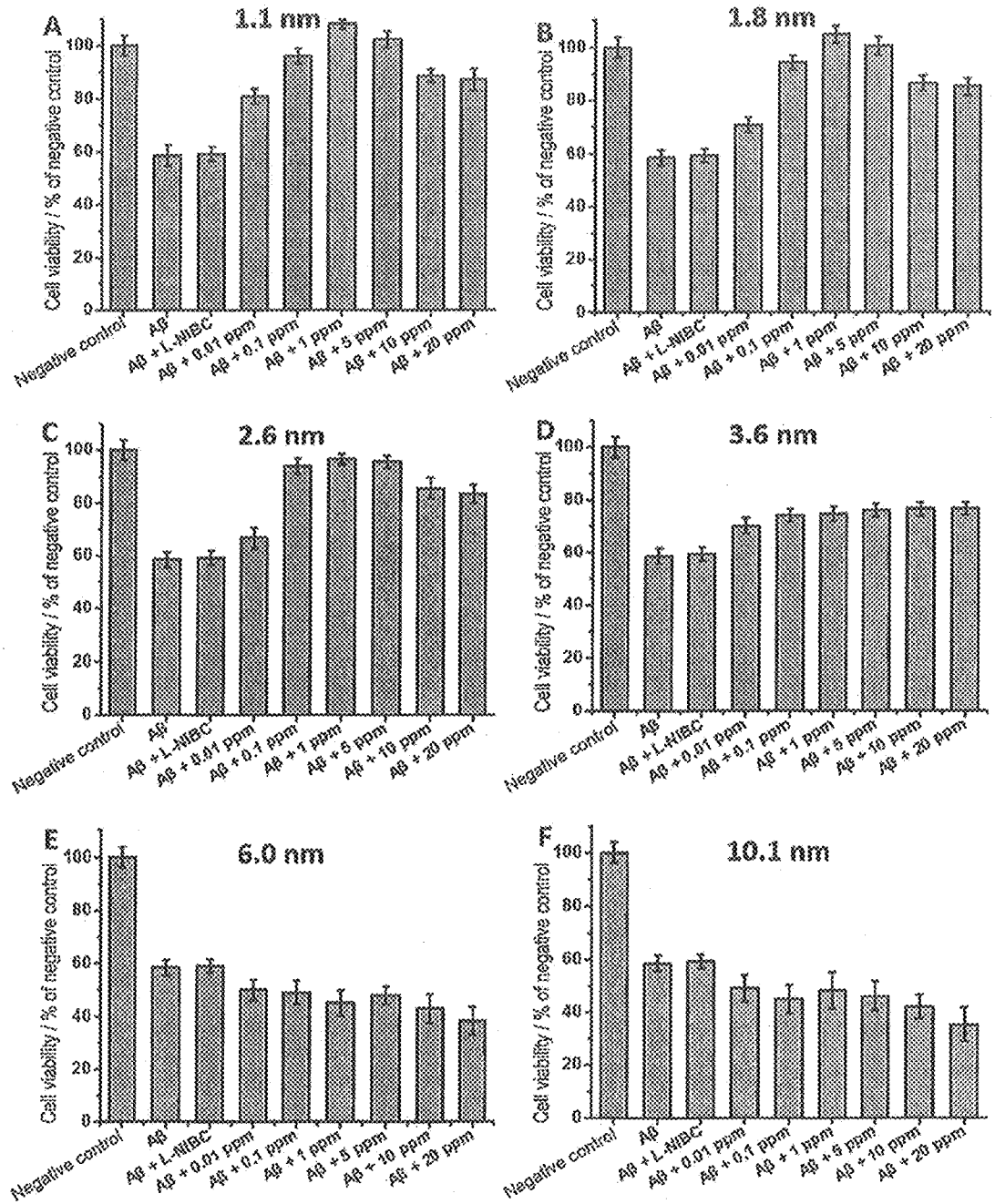
FIG. 6 shows diagrams showing the effects of ligand L-NIBC-modified gold nanoparticles or AuCs of different particle sizes and different concentrations on the cell viability of Aβ-induced AD cell model.
Figure 7:
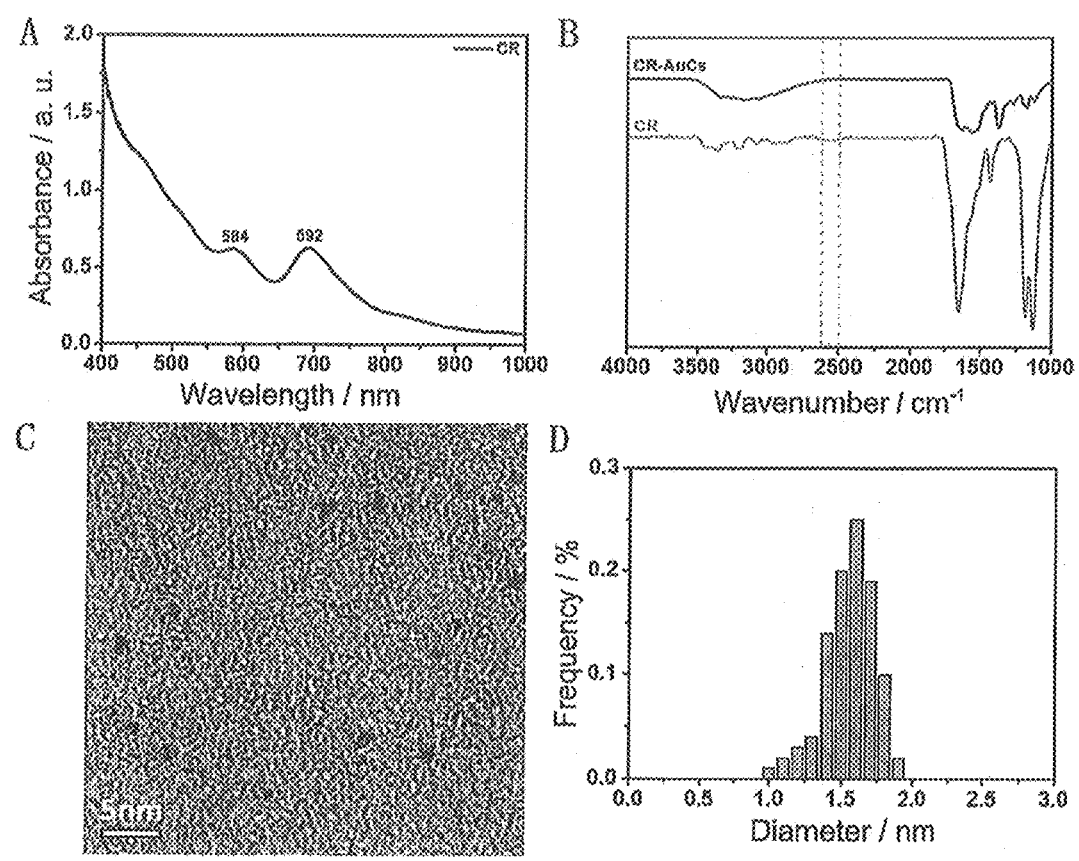
FIG. 7 shows UV, infrared, TEM and particle size distribution diagrams of AuCs modified with ligand CR (CR-AuCs).
Figure 8:
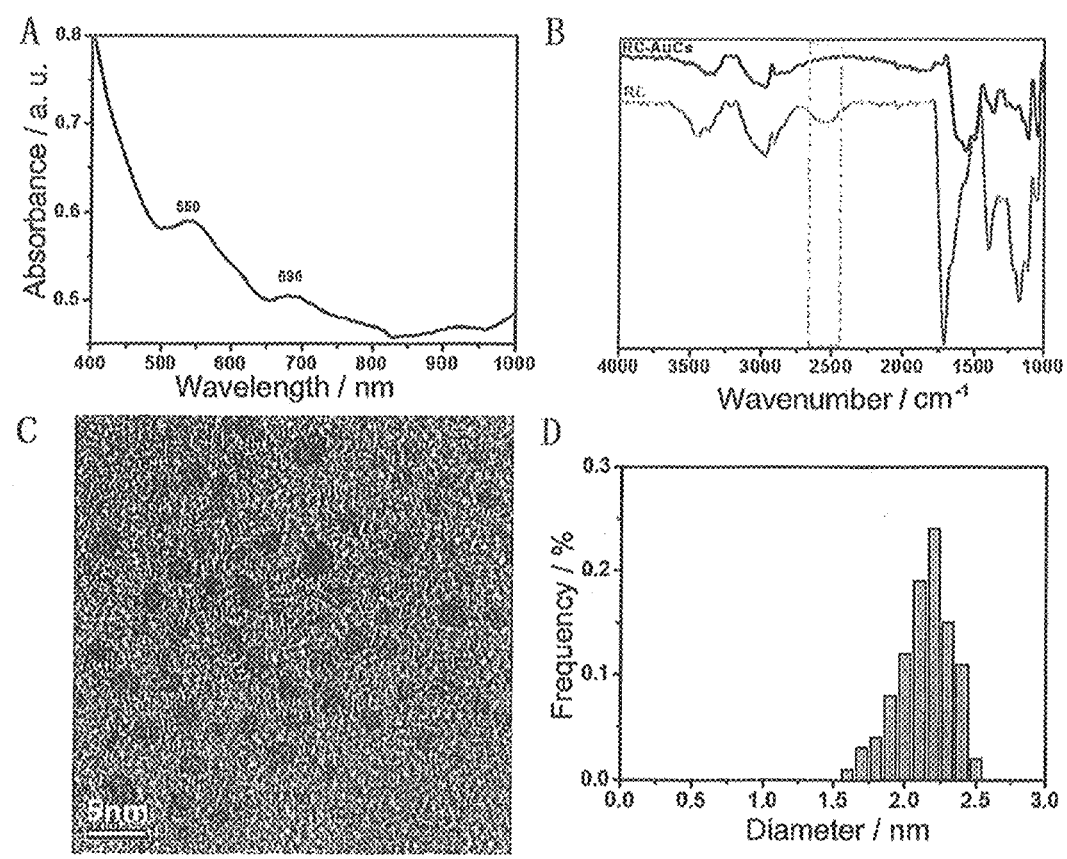
FIG. 8 shows UV, infrared, TEM and particle size distribution diagrams of AuCs modified with ligand RC (RC-AuCs).
Figure 9:
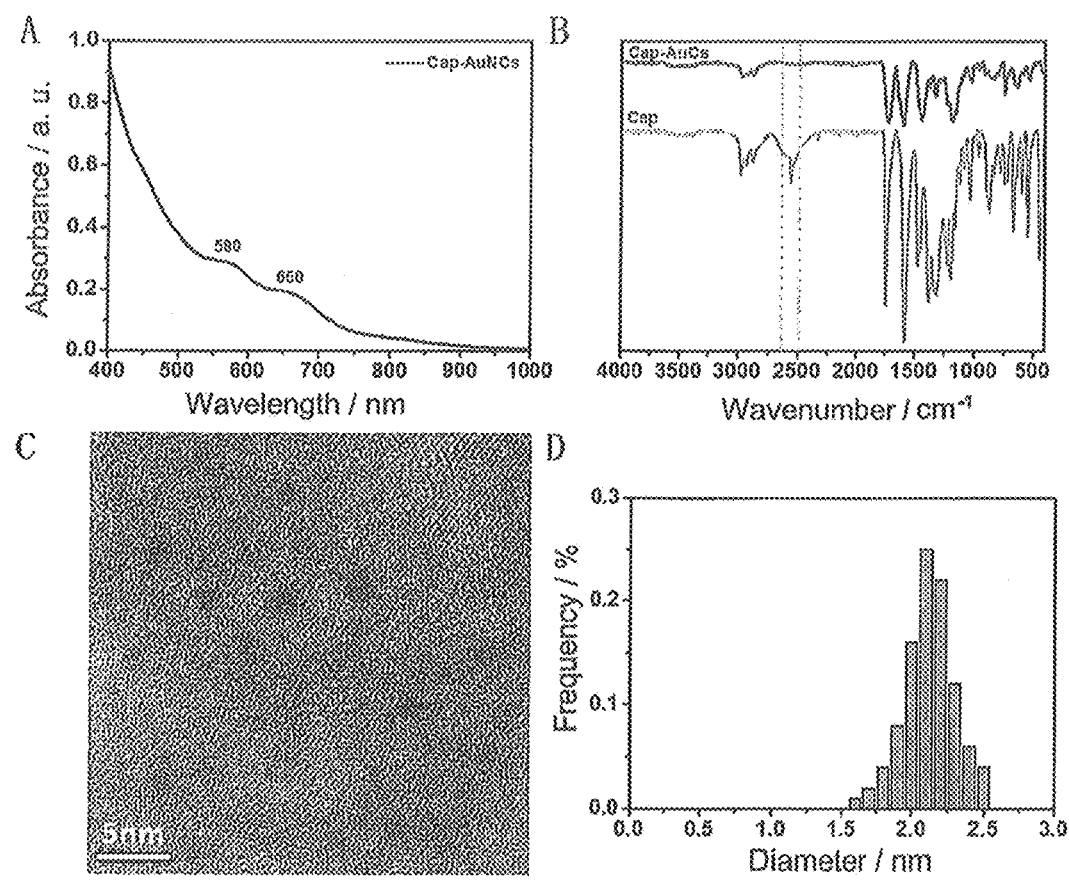
FIG. 9 shows UV, infrared, TEM and particle size distribution diagrams of AuCs modified with ligand 1-[(2S)-2-methyl-3-thiol-1-oxopropyl]-L-proline (i.e., Cap).
Figure 10:
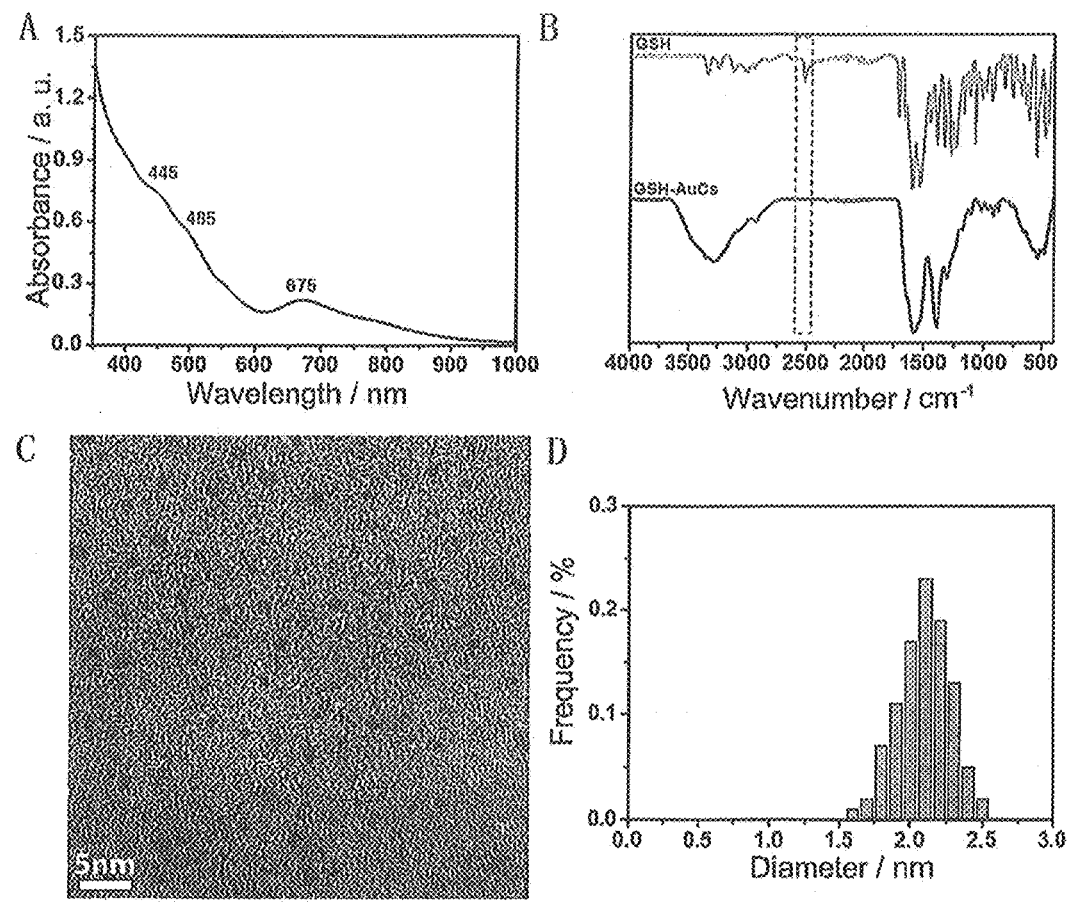
FIG. 10 shows UV, infrared, TEM and particle size distribution diagrams of AuCs modified with ligand GSH (GSH-AuCs).
Figure 11:
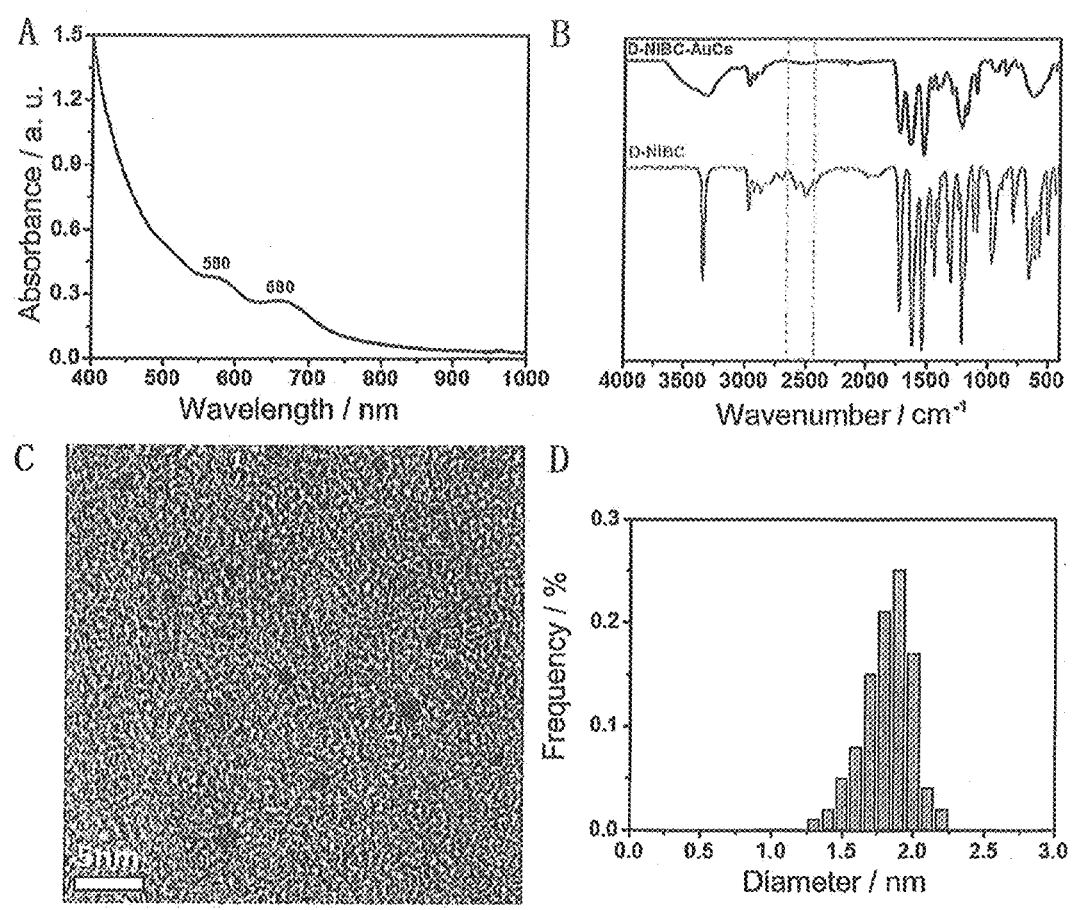
FIG. 11 shows UV, infrared, TEM and particle size distribution diagrams of AuCs modified with ligand D-NIBC (D-NIBC-AuCs).

L-NIBC-modified AuCs in Embodiment 2 was taken for example, L-NIBC-modified gold nanoparticles were compared with AuCs and the results are shown in FIG. 6.

Panels A-C of FIG. 6 respectively shows the effects of L-NIBC-modified AuCs with a particle size of 1.1 nm, 1.8 nm or 2.6 nm at different concentrations on the cell viability in Aβ induced AD cell model; panels D-F respectively shows the effects of L-NIBC-modified gold nanoparticles with a particle size of 3.6 nm, 6.0 nm or 10.1 nm at different concentrations on the cell viability of the Aβ induced AD cell model.

As shown in FIG. 6, the addition of L-NIBC only did not improve cell viability. L-NIBC-modified AuCs with different sizes (the average sizes were 1.1, 1.8 and 2.6 nm respectively) raised the cell viability from nearly 60% to above 95% in Aβ-induced AD cell model (P values were all less than 0.05, in panels A-C of FIG. 6) even at a very low dose (0.1-1 ppm for instance). L-NIBC-modified gold nanoparticles in an average diameter of 3.6 nm raised the cell viability to some extent with the increase of concentrations in AD cell model (panel D of FIG. 6), but not obviously (P>0.05). L-NIBC-modified gold nanoparticles in average diameters of 6.0 nm and 10.1 nm respectively did not have effect on cell viability (panels E and F of FIG. 6). The above results indicated that L-NIBC-modified AuCs had a significant medicinal efficacy on Aβ-induced AD cell model, while L-NIBC-modified gold nanoparticles had no obvious efficacy.

Experiments on AuCs modified with other ligands listed in Table 1 in various sizes were conducted in this embodiment. The results also indicated that ligand-modified AuCs significantly improved the cell viability in Aβ-induced AD cell model. It was indicated that AuCs modified with different ligands had excellent therapeutic effects on AD at least at the cell model level, which could be classified into the AuCs-containing substances as defined in the present invention and be used for AD treatment.

Embodiment 5: Experiment of AD Transgenic Mouse Model

Experiment 1

1) 1.0 g of AuCs modified with ligands listed in Table 1 were weighed respectively, and dissolved in 100 mL water as stock solutions, and stored at 4° C. for future use. A small volume of the stock solutions was taken and diluted in water before use.

2) 180 B6/J-Tg(APPswe,PSEN1de9)85Dbo/MmNju strain transgenic mice (purchased from the Model Animal Research Center of Nanjing University) were randomly divided into three groups, 60 mice per group, including a control group, a low dose group and a high dose group. When the mice were 100 day old, mice in the control group were fed normally everyday, mice in the low dose group were orally administered with 200 μL of 0.5 g/L AuCs in water a day, and mice in the high dose group were orally administered with 200 μL of 2 g/L AuCs in water a day.

3) The mice in the control group, low dose group and high dose group were randomly divided into 7 batches respectively: When the mice were 140 days, 160 days, 180 days, 200 days, 230 days, 260 days and 290 days old respectively, maze experiment, open field experiment, and new object recognition experiment were adopted to research the changes of mice in learning and memory behaviors. In the first four batches, 6 mice in each group; and in the last three batches, 6-8 mice in each group (considering that there was a certain mortality rate in the feeding process of mice, the same below).

4) After the behavioral researches of above each batch mice, the content of Aβ in the blood was detected: blood was collected from the orbital venous plexus, and the content of Aβ and Aβ aggregation were detected by serum Elisa method.

5) After the content of Aβ in the blood of above each batch mice was detected, the Aβ amyloid deposition distributing in the hippocampus was detected: the mice were anesthetized after extraction of ocular blood, they were fixed via heart perfusion. The whole brains of mice were collected and sedimentated by gradient in sucrose. Then the brains were freezed and sectioned. The distribution of Aβ amyloid deposits in the hippocampus was examined by immunohistochemistry.

The results showed that the ligand-modified AuCs provided in the present invention could significantly improve the cognitive behavior of AD transgenic mice, and inhibit the formation of senile plaques in the brain and the development of the disease, which may be used to treat AD as AuCs-containing substances.

Experiment 2

1. 1.0 g AuCs modified with ligands listed in Table 1 were weighed respectively, were dissolved in 100 mL water as stock solutions stored at 4° C. for future use. A small volume of the stock solutions was taken and diluted in water before use. The stock solutions were prepared once two weeks.

2. 90 B6/J-Tg(APPswe,PSEN1de9)85Dbo/MmNju strain transgenic mice (purchased from the Model Animal Research Center of Nanjing University) were randomly divided into three groups: a model control group, a low dose group and a high dose group, 30 mice per group (considering that the transgenic mice of this strain had about 30% mortality in the feeding process, in order to ensure sufficient mice in the late of this experiment, there were more mice in the initial than in the late of this experiment). When the mice were 100 days old, mice in the model control group were fed normally everyday, mice in the low dose group and high dose group were orally administered with AuCs solution at a dose of 5 mg/kg body weight and 20 mg/kg body weight respectively by intraperitoneal injection once every two days.

Figure 13:
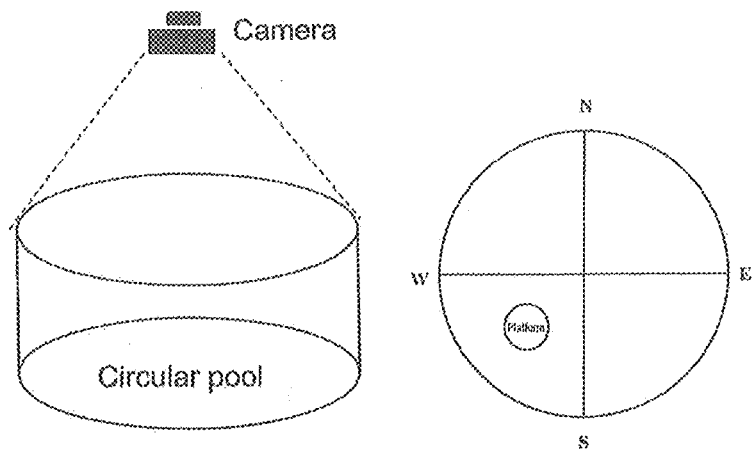
FIG. 13 shows a schematic diagram of a water maze experiment device in Embodiment 5.

3. The cognitive behavior of mice was tested using water maze experiment Morris water maze (MWM) experiment is the one to force tested animal to swim and learn to find the platform hidden in the water. MWM is mainly used to test the tested animal's learning and memory abilities of the spatial positions and direction perception, which is widely adopted in the research of AD medication development and evaluation. Shorter escape latency, more times of crossing the platform after removal, longer swimming distance in the target quadrant, and longer staying in the target quadrant of the mice, mean that the mice have a better memory ability of spatial position and direction perception. After 150 days of administration, the behavior of each mouse was tested in Morris water maze experiment. This experimental method refers to the literature (C. V. Vorhees, M. T. Williams, Nature Protocols 2006, 1, 848). Details were as follows:

(1) Positioning navigation experiment: The MWM test system consisted of a circular pool and an automatic video and analysis system. The cameras above the pool were connected to a computer (as shown in FIG. 13). The water maze consisted of a circular pool in a diameter of 120 cm and a height of 60 cm, and a platform in a diameter of 9 cm. The liquid level was 0.5 cm higher than the platform and the water temperature was at 22±0.5° C. White pigment was used to dye water to milky white. The positioning experiment was used to measure the learning and memory abilities of mice in water maze, which lasted for 4 days. As shown in FIG. 13, the water maze was divided as a cross into four quadrants in the four directions of East (E), West (W), South (S) and North (N). The platform was placed in the middle of the SW quadrant, position of which was fixed throughout the experiment During training the mice were gently put into water from ½ radian in different quadrants, with heads facing the pool wall and near the inner wall. The time that the mice spent in climbing onto the hidden platform (escape latency) was recorded by a camera tracking system, or the experiment is stopped when the record time reached 60 s. The mice were allowed to stay on the platform for 30 s after climbing onto the platform. If the mice failed to find the platform within 60 s (the escape latency was recorded as 60 s in this case), the experimenters would guide the mice to climb onto the platform and let them stay on the platform for 30 s. After the experiment, every mouse was moved away and wiped dry gently. Each mouse was trained 4 times a day for four consecutive days, with 15-20 min intervals between training sessions.

(2) Spatial probe test: After finishing the training on the 4th day, the platform was removed on the 5th day, the mice were gently put into the water from the midpoint of the NE arc (the farthest point of the platform) facing the pool wall, the 60 s movement orbits of the mice were recorded by camera, and the times of mice crossing the platform, time of stay in the target quadrant and the swimming distance in the target quadrant were analyzed by a software.

4. Immunohistochemistry experiment is used to detect the distribution of amyloid deposition in the hippocampus and cerebral cortex Aβ(1-40) and Aβ(1-42). The pathological deposition of Aβ outside neurons in the cerebral cortex and hippocampus is the main pathological feature of AD. Among them, Aβ(1-40) and Aβ(1-42) are important components of senile plaques in the brain, which are neurotoxic and can cause progressive cognitive dysfunction and memory loss. In this experiment, the changes of Aβ(1-40) and Aβ(1-42) plaque formation in the hippocampus and cerebral cortex were examined by immunohistochemistry.

Specific method: After the mice were administered consecutively for 100 days and 150 days, 10-12 mice were taken from each group to do immunohistochemistry of hippocampus and cerebral cortex. Here, the mice with 150 days of administration were those had completed the MWM experiment After the mice were anesthetized by intraperitoneal injection of 5% chloral hydrate (10 μL/g), the limbs were fixed on the experiment table, and the chests were opened to expose the hearts fully. Pay attention to not cut the livers during thoracotomy. The left ventricles were washed with 50 mL 0.1 mol/L PBS for 5 min firstly to remove blood, and then 0.1 mol/L PBS containing 4% paraformaldehyde was used for perfusion and fixation for 6 min. After perfusion and fixation, the brains were removed and placed in 4% paraformaldehyde at 4° C. and were fixed overnight. The tissues were dehydrated with 10%, 20% and 30% sucrose solution by gradient in turn and stored at −80° C. for future use. The tissues were embedded with paraffin. The midbrain hippocampus and cerebral cortex (8 μm thick) were sliced in reference to mouse brain map and used for immunohistochemical staining. The steps were as follows: the frozen 8 μm thick slices were kept at room temperature for 30 min, fixed in 4° C. acetone for 20 min, washed with PBS for three times (5 min each time), and then incubated in 3% $H_2O_2$ for 10 min to eliminate peroxidase activity. After washed with PBS for three times (5 min a time), the slices were blocked with 10% normal goat serum for 40 min at room temperature (the slices used for Aβ(1-42) immunohistochemistry were incubated in 10% formic acid for 10 min before blocking to repair antigenic activity). The serum was poured out, anti-Aβ(1-40) (ab20068, 1:20 dilution) or anti-Aβ(1-42) working fluid (ab12267, 1:200 dilution) were added into the slices, and were incubated for 2 h at room temperature, were washed with PBS for three times (5 min a time). Horseradish enzyme labeled streptavidin (diluted with PBS) was added dropwise to the secondary antibody working solution, and was incubate at room temperature for 1 h. After washed with PBS for three times (5 min a time), nickel sulfate enhanced DAB blue reaction method was adopted for coloration for 10 min. When the positive product was dark blue and the background was clear, it was rinsed with distilled water for 3 times to stop coloration. After counter-stained with hematoxylin for 1 min, it was rinsed with tap water, was dried in a ventilated place, and sealed with neutral gum. The number of Aβ plaques in the entire hippocampus and cerebral cortex was observed and counted by a confocal microscope. Each sample included two slices containing both left and right ventricles as parallel samples. The average value was calculated for statistical analysis. All data were processed by SPSS software (SPSS 21), and undergone t test or one-way analysis of variance. $P<0.05$ meaned that the difference is statistically significant.

Figure 14:
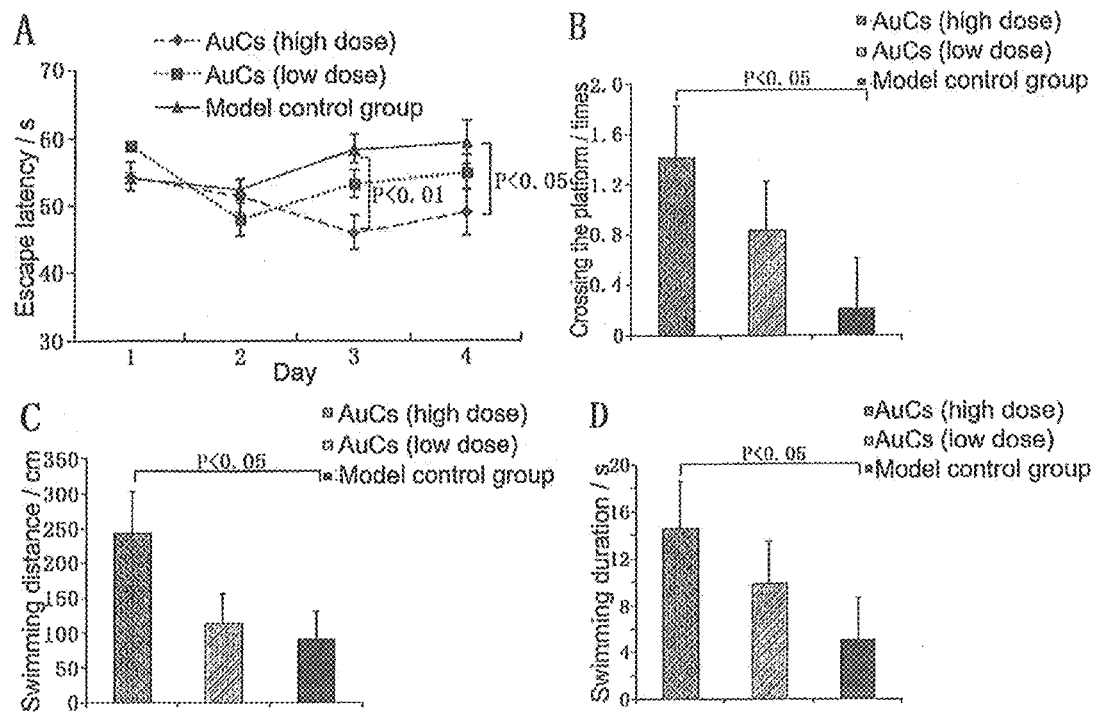
FIG. 14 shows diagrams showing the effect of an AuCs-containing substance on the cognitive behavior (day 150 of administration) of APP/PS1 double transgenic C57BL/6 mouse model.

L-NIBC-modified AuCs with an average size of 1.8 nm in Embodiment 2 was taken for example, the result of the water maze experiment after 150 days of administration was shown in FIG. 14. The result indicated that there was no statistical difference between the mice in the model control group and in the high dose and low dose groups in escape latency on day 1-2 of the positioning navigation test ($P>0.05$, n=10-12/group) (panel A of FIG. 14). With the increase of training time, the escape latency of the mice in the high dose group was obviously lower than that in the model group on day 3 and day 4 ($P<0.01$ and $P<0.05$), and the escape latency in the low dose group was lower than that in the model group, but no statistical difference ($P>0.05$, see panel A of FIG. 14). After mouse positioning navigation experiment was completed, the platform was removed and started space search experiment. The results showed that compared with the mice in the model control group, the mice in the high dose group had significant increase in the times of crossing the platform and the swimming distance in the target quadrant ($P<0.05$), and the time of staying in the target quadrant was also significantly increased, too ($P=0.05$). Compared with the mice in the model control group, the mice in the low dose group showed increase in the times of crossing the platform, the swimming distance in the target quadrant and the time of stay in the target quadrant, but no significant difference ($P>0.05$) (panels B-D of FIG. 14). The above results indicated that after 150 days' administration of AuCs, AuCs significantly improved the ability of APP/PS1 mice to learn and remember spatial position and sense of direction. And this effect was dose dependent.

The results of the immunohistochemistry experiment for detecting the distribution of amyloid deposition of Aβ(1-40) and Aβ(1-42) in the hippocampus and cerebral cortex are shown in FIG. 15-FIG. 18.

Figure 15:
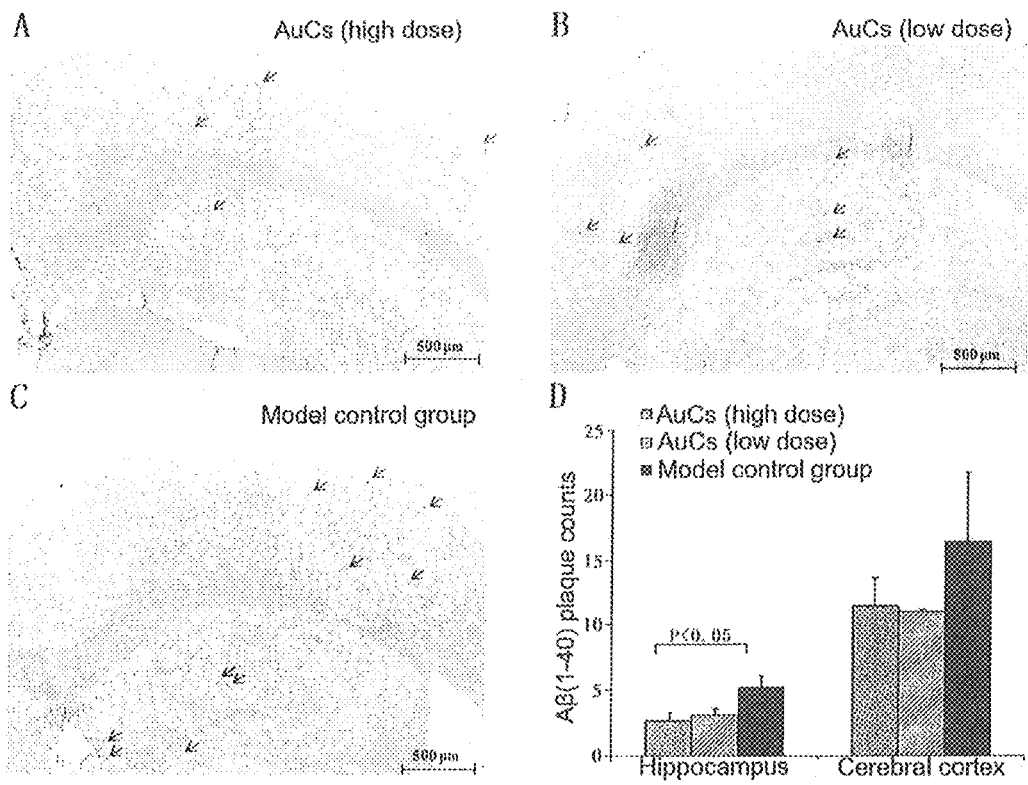
FIG. 15 shows diagrams showing the effect of an AuCs-containing substance on the expression of Aβ (1-40) in the hippocampus and cerebral cortex of mice in APP/PS1 double transgenic C57BL/6 mouse model (day 100 of administration).
Figure 16:
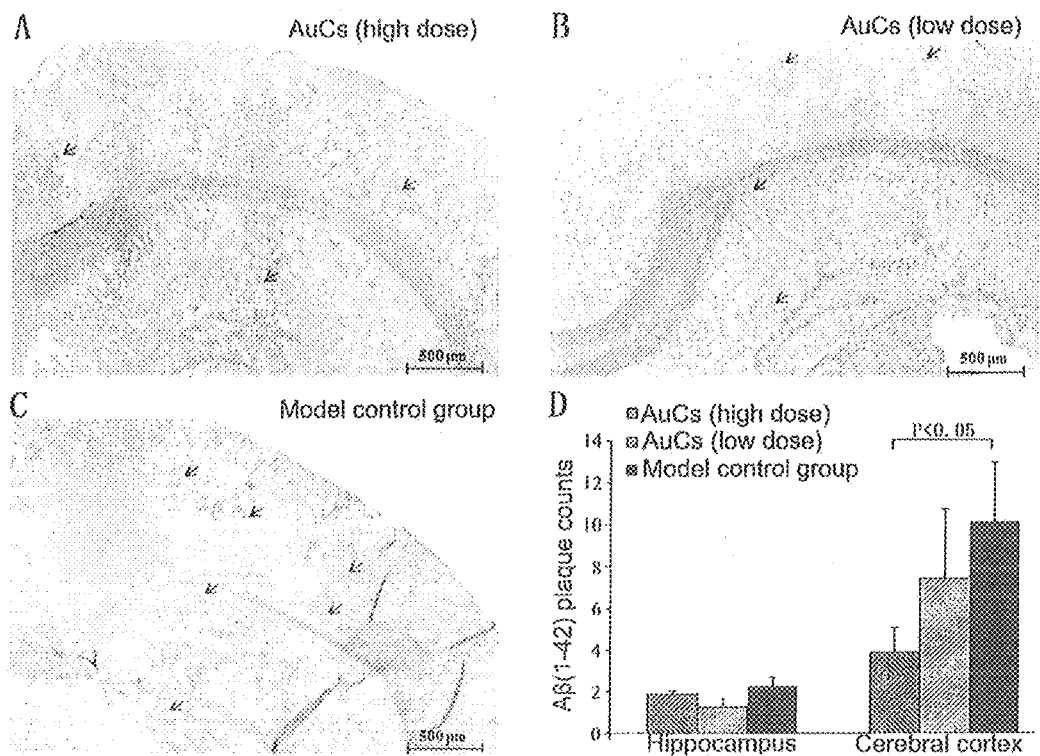
FIG. 16 shows diagrams showing the effect of an AuCs-containing substance on the expression of Aβ (1-42) in the hippocampus and cerebral cortex of mice in APP/PS1 double transgenic C57BL/6 mouse model (day 100 of administration).
Figure 17:
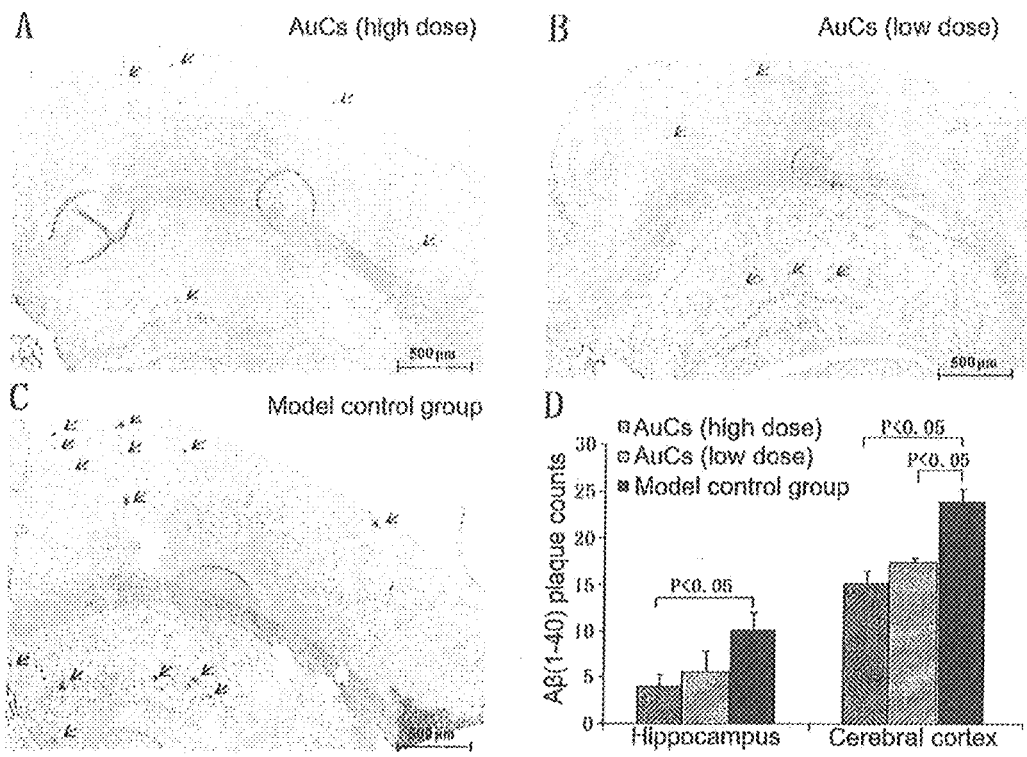
FIG. 17 shows diagrams showing the effect of an AuCs-containing substance on the expression of Aβ (1-40) in the hippocampus and cerebral cortex of mice in APP/PS1 double transgenic C57BL/6 mouse model (day 150 of administration).

Panels A, B and C of FIG. 15 were results of typical immunohistochemical slices of the hippocampus and cerebral cortex of Aβ(1-40) in the high dose group, low dose group and model control group on the 100th day of administration. Panel D of FIG. 15 was the statistical result. The experimental results indicated that compared with the model control group, mice in the high dose group had significantly reduced Aβ(1-40) plaques in the hippocampus (44.6±12.2%, $P<0.05$) on the $100^{th}$ day of administration, but not in the cerebral cortex (P>0.05). The low dose group did not have a significant effect on the formation of Aβ(1-40) plaques in the hippocampus and cerebral cortex (P>0.05). FIG. 16 showed the corresponding results of Aβ(1-42). It indicated that the administration at a high dose could significantly reduce the formation of Aβ(1-42) plaques in the cerebral cortex (reduced by 61.5±11.4%, P<0.05), but not in the hippocampus (P>0.05). The administration at a low dose does not have a significant effect on the formation of Aβ(1-42) plaques in the hippocampus and cerebral cortex (P>0.05). These results indicated that on the 100th day of administration, AuCs had shown a significant inhibitory effect on the formation of Aβ(1-40) and Aβ(1-42) plaques, and this effect showed an obvious dose-dependent relationship.

With the increase of administration time and age of mice, the formation of Aβ(1-40) and Aβ(1-42) plaques in the hippocampus and cerebral cortex of mice increased significantly in the model control group with 150 days of administration compared with 100 days of administration. To be specific, Aβ(1-40) increased 57.2±7.2% in the hippocampus (P<0.05), and 49.1±19.6% in the cerebral cortex (P<0.05), and Aβ(1-42) increased 74.4±7.0% in the hippocampus (P<0.05), and 65±11.1% in the cerebral cortex (P<0.05). It was suggested that the older the model mice were, the greater the influence on memory and cognitive functions might be. Panels A, B and C of FIG. 17 were results of typical immunohistochemical slices of the hippocampus and cerebral cortex of Aβ(1-40) in the high dose group, low dose group and model control group on the 150th day of administration respectively. Panel D of FIG. 17 was the statistical result. The results indicated that in the high dose group, Aβ(1-40) decreased obviously in both the hippocampus and cerebral cortex of mice (reduced by 59.0±11.1%, P<0.05 in the hippocampus; and 36.4±4.5%, P<0.05 in the cerebral cortex), while administration at a low dose did not have a significant effect on the formation of Aβ(1-40) plaques in the hippocampus (P>0.05), but significantly reduced Aβ(1-40) plaques in the cerebral cortex (reduced by 26.9±2.1%, P<0.05). It was indicated AuCs had a significant inhibitory effect on the formation of Aβ(1-40) plaques on the 150th day. This effect also showed a dose-dependent relationship. In addition, SPSS software was used to analyze the correlation between the numbers of Aβ(1-40) plaques and the times of crossing the platform in the 150-day water maze experiment. The analysis revealed that the numbers of Aβ(1-40) plaques in the hippocampus and cerebral cortex was significantly negative correlative with the times of crossing the platform (the hippocampus: R=−0.848, P<0.01; cerebral cortex: R=−0.802, P<0.05). This result further supported the correlation between the reduction of Aβ(1-40) plaques in the hippocampus and cerebral cortex induced by AuCs administration and the improvement of memory and learning abilities of mice induced by AuCs administration.

Figure 18:
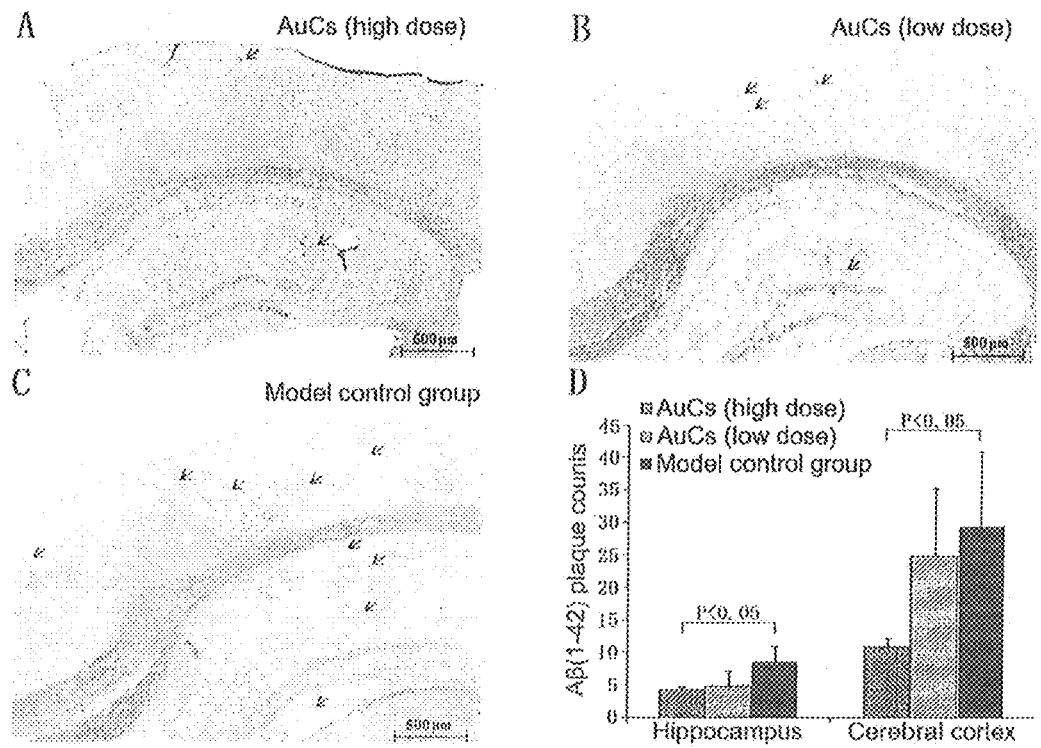
FIG. 18 shows diagrams showing the effect of an AuCs-containing substance on the expression of Aβ (1-42) in the hippocampus and cerebral cortex of mice in APP/PS1 double transgenic C57BL/6 mouse model (day 150 of administration).

FIG. 18 shows the corresponding results of Aβ(1-42) upon 150-day AuCs administration. The results indicated that the AuCs administration at a high dose obviously inhibited the formation of Aβ(1-42) plaques in the hippocampus and cerebral cortex (reduced by 51.1±6.7%, P<0.05 in the hippocampus; and 62.8±4.6%, P<0.05 in the cerebral cortex). Administration at a low dose did not have an obvious effect on the formation of Aβ(1-42) plaques in the hippocampus and cerebral cortex of mice (P>0.05). It was indicated that AuCs had a significant inhibitory effect on the formation of Aβ(1-42) plaques on the 150th day. This effect showed a dose-dependent relationship. The correlation statistics analysis by SPSS revealed that the numbers of Aβ(1-42) plaques in the hippocampus and cerebral cortex were significant negative correlative with the times of crossing the platform (hippocampus: R=−0.794, P<0.05; cerebral cortex: R=−0.802, P<0.05). This result further supported the correlation between the reduction of Aβ(1-42) plaques in the hippocampus and cerebral cortex induced by AuCs administration and the improvement of memory and learning abilities of mice induced by AuCs administration.

In summary, AuCs could significantly improve the cognitive behavior of AD model mice, and inhibit the formation of Aβ(1-40) and Aβ(1-42) plaques in the hippocampus and cerebral cortex, thus AuCs could inhibit the development of the illness condition of sick mice, and be used to prevent and treat AD as AuCs-containing substances.

The AuCs modified with other ligands listed in Table 1 had similar effects, so they were not described in details here.

Embodiment 6: Experiment of In Vitro α-Syn Aggregation Kinetics

This embodiment validated the functions of ligand-modified AuCs through in vitro α-syn aggregation kinetics experiment, and compared it with the effect of ligand molecules on α-syn aggregation kinetics when used alone, so as to prove that this function is from AuCs other than ligand.

Thioflavin T (abbreviation: ThT) is a dye for dyeing amyloid fibers specifically. When it is incubated together with monomers of polypeptides or proteins, its fluorescence does not change much. When it encounters amyloid polypeptide or protein with a fiber structure, it will immediately couple with the amyloid polypeptides or proteins and its fluorescence intensity will increase exponentially. For this reason, ThT is widely used as markers to monitor amyloidosis of peptides or proteins. This embodiment utilizes ThT fluorescent labeling method to monitor the kinetics process of fibrosis aggregation of α-syn with the existence of AuCs. The specific experiment method was as follows:

Pretreatment of α-syn monomers: Freeze-dried powder (Bachem Corp.) of α-syn was dissolved in HFIP to obtain a 1 g/L α-syn solution. The solution was incubated at room temperature for 2-4 h after sealing, then blowed to dry HFIP by high-purity nitrogen in a fume hood. Lastly the dried α-syn was dissolved in 200 μL DMSO, after sealing, the solution was kept in a refrigerator at −20° C. for no more than one week for future use. Before use, the DMSO solution of α-syn was diluted with plenty of phosphate buffer solution (PBS, 10 mM, pH=7.4) till the concentration of α-syn reached 20 μM to obtain an α-syn PBS solution. All the α-syn PBS solutions in the experiment were prepared freshly.

Sample preparation and detection: Ligand-modified AuCs in different concentrations listed in Table 1 were added to 35 μM α-syn PBS solutions respectively, and incubated continuously in a 96-well plate at 37° C., by ThT fluorescent labeling method, and were monitored the fluorescence intensity by microplate reader once every 10 minutes. The kinetic process of α-syn aggregation was characterized through the change of fluorescence intensity of ThT. L-NIBC-modified AuCs with a particle size of 1.8 nm prepared in Embodiment 2 were taken for example as experiment groups. L-NIBC molecules uncombined with AuCs were used as a ligand control group. Four concentrations of AuNCs are adopted, which were: 0 ppm (containing α-syn only, not containing AuCs or L-NIBC, as a model control group), 1.0 ppm, 5.0 ppm and 10.0 ppm respectively. L-NIBC molecules in two concentrations were used, which were: 1.0 ppm and 10.0 ppm respectively.

Figure 19:
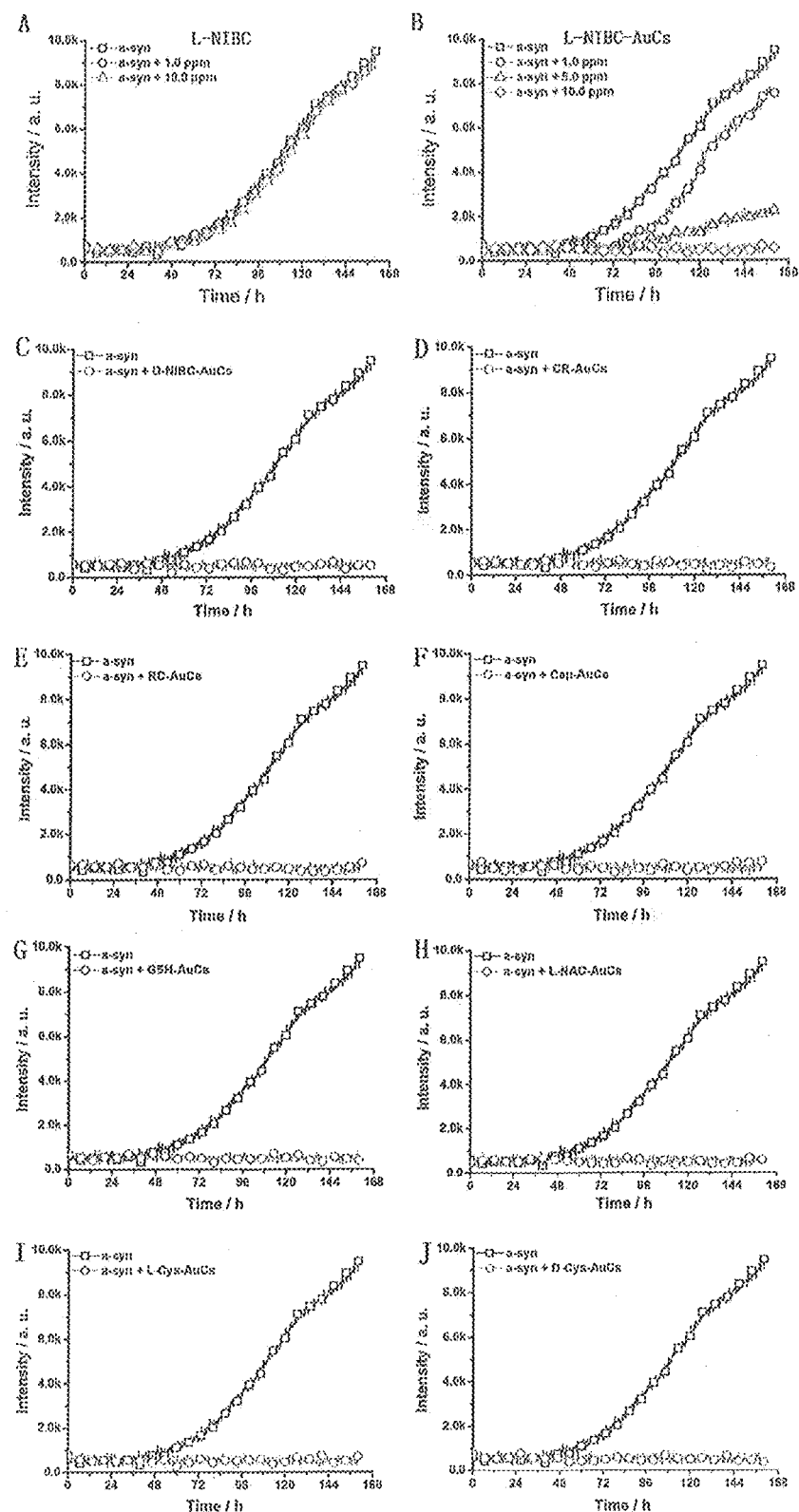
FIG. 19 is a diagram showing the effect of a substance containing AuCs on α-syn fibrosis kinetics.

The results were shown in FIG. 19. The results indicated that in the incubation process of 35 μM α-syn at 37° C., ThT-labeled fluorescence intensity increased rapidly from the 48th hour. It was demonstrated that α-syn aggregation and fibrosis happened. This was consistent with the result reported in the literature (V. N. Uversky, J. Li, P. Souillac, L S. Millett, S. Doniach, R. Jakes, M. Geodert, A. L. Fink, Journal of Biological Chemistry 2002, 277, 11970). The result of the ligand control group indicated that using L-NIBC only did not have an obvious effect on kinetics of α-syn aggregation (panel A of FIG. 19). In the experimental group with addition of AuCs in a low concentration (such as: 1.0 ppm and 5.0 ppm), ThT-labeled fluorescence intensity decreased significantly compared with the model control group and ligand control group without the addition of AuCs, and the starting time delayed obviously (panel B of FIG. 19). It was suggested that the addition of AuCs could significantly inhibit α-syn aggregation and fibrosis. When AuCs concentration reached 10 ppm, ThT-labeled fluorescence intensity remained near the base line without any increase throughout the 168 hours of the experiment (panel B of FIG. 19). It was suggested that when AuCs concentration was high enough, α-syn aggregation and fibrosis could be inhibited completely.

In this embodiment, AuCs modified with other different ligands listed in Table 1 were also studied. For example, panels C-J of FIG. 19 showed the inhibitory effects of AuCs modified with D-NIBC, CR, RC, 1-[(2S)-2-methyl-3-thiol-1-oxopropyl]-L-proline (Cap), GSH, N-acetyl-L-cysteine (L-NAC), L-cysteine (L-Cys) and D-cysteine (D-Cys) (the dose were all 10 ppm) on α-syn aggregation and fibrosis. A similar phenomenon was also observed for AuCs modified with different ligands, and the same conclusion could be reached: These ligands per se could not influence α-syn aggregation and fibrosis, while ligand-modified AuCs had an excellent inhibitory effect on α-syn aggregation and fibrosis. When the concentration reached 10 ppm, an effect of complete inhibition could all be achieved. The minimum concentration needed for complete inhibition varies slightly with different ligands. Likewise, these ligand-modified AuCs were classified into AuCs-containing substances defined in the present invention. Other AuCs listed in Table 1 had similar effects. Only the concentrations of AuCs needed for complete inhibition of α-syn aggregation and fibrosis were different. It would not be described in details.

Embodiment 7: Experiment of MPP+ Induced PD Cells (SH-sy5y) Model

Experiment 1

The experiment uses cell viability as an indicator; the test results obtained from CCK-8 method reflect the resistance efficacy of ligand-modified AuCs or gold nanoparticles against the toxic effect of MPP$^+$ (a common-used neurotoxin) in SH-sy5y nerve cell model of PD, so as to demonstrate their neuroprotection effect on PD. The MPP$^+$ induced PD cell model is established according to the description in literatures (Cassarino, D S; Fall, C P; Swerdlow, R H; Smith, T S; Halvorsen, E M; Miller, S W; Parks, J P; Parker, W D Jr, Bennett, J P Jr. Elevated reactive oxygen species and antioxidant enzyme activities in animal and cellular models of Parkinson's disease. Biochimica et biophysica acta. 1997.1362.77-86). Specific method was as follows:

1) SH-sy5y cells in the logarithmic growth phase were diluted with complete medium to get a cell suspension in a cell density of $5 \times 10^4$/mL. The suspension was inoculated 200 μl per well into a 96-well plate, and cultivated in an incubator with 5% $CO_2$ at 37° C. A sample was added when the cells attached to the wells.

2) 100 μL ligand-modified AuCs samples (listed in Table 1) or ligand-modified gold nanoparticles samples with different particle sizes and different concentrations, were dissolved in maintenance medium, were added as the first groups to make the final concentrations be 0.01 ppm, 0.1 ppm, 1 ppm, 5 ppm, 10 ppm and 20 ppm respectively. The first groups were the administration groups. After 2 hours of pretreatment on ligand-modified AuCs or gold nanoparticles, MPP$^+$ (final concentration was 1 mM) was added to the administration groups and the cell control group respectively, simultaneously, a blank control group was the one not containing SH-sy5y cells, a negative control group was the one containing SH-sy5y cells but without AuCs or gold nanoparticles and MPP$^+$, a cell control group was the one containing SH-sy5y cells and 1 mM MPP$^+$ only, and a ligand control group was the one containing SH-sy5y cells and 1 mM MPP+ and corresponding ligand molecules (final concentration was 20 ppm), then the samples in every groups were incubated at 37° C. for 24 h, were centrifuged to remove the culture medium, 100 μL maintenance medium containing 10% CCK-8 was added into each well, and continued to be incubated for 4 h, and then the absorbances of each well were measured at 450 nm to reflect the pre-protective and curative effects of ligand-modified AuCs against MPP$^+$ lesion.

The same steps were adopted to carry out the experiments for AuCs and gold nanoparticles modified with different ligands. The results indicated that the ligand-modified AuCs provided in the present invention had a neuroprotective effect on PD. This effect was also originated from AuCs, rather than the ligand. They can be used as substances containing AuCs to resist PD.

Experiment 2

The experiment uses cell viability as an indicator. The test results obtained from CCK-8 method reflect the resistance efficacy of ligand-modified AuCs or gold nanoparticles against the toxic effect of MPP$^+$ (a common-used neurotoxin) in SH-sy5y nerve cell model of PD, demonstrate their neuroprotection effect on PD. The MPP$^+$ induced PD cell model is established according to the description in the reference (D. S. Cassarino, C. P. Fall, R H. Swerdlow, T. S. Smith, E. M. Halvorsen, S. W. Miller, J. P. Parks, W. D. Jr. Parker, J. P. Jr. Bennett, Biochimica et Biophysica Acta 1997, 1362, 77). Specific method:

1) SH-sy5y cells in the logarithmic growth phase were diluted with complete medium to get a cell suspension in a cell density of $5 \times 10^4$/mL. The suspension was inoculated 200 μl per well into a 96-well plate, and cultivated in an incubator with 5% $CO_2$ at 37° C. A sample was added when the cells attached to the wells.

2) 100 μL ligand-modified AuCs samples (listed in Table 1) or ligand-modified gold nanoparticles samples with different particle sizes and different concentrations, were dissolved in maintenance medium, were added as the first groups to make the final concentrations be 0.01 ppm, 0.1 ppm, 1 ppm, 5 ppm, 10 ppm and 20 ppm respectively. The first groups were the administration groups. After 2 hours of pretreatment on ligand-modified AuCs or gold nanoparticles, MPP$^+$ (final concentration was 1 mM) was added to the administration groups and the cell control group respectively, simultaneously, a blank control group was the one not containing SH-sy5y cells, a negative control group was the one containing SH-sy5y cells but without AuCs or gold nanoparticles and MPP$^+$, a cell control group was the one containing SH-sy5y cells and 1 mM MPP$^+$ only, a AuCs control group, and a ligand control group was the one containing SH-sy5y cells and 1 mM MPP$^+$ and corresponding ligand molecules (final concentration was 20 ppm), then the samples in every groups were incubated at 37° C. for 24 h, were centrifuged to remove the culture medium, 100 µL maintenance medium containing 10% CCK-8 was added into each well, and continued to be incubated for 4 h, and then the absorbances of each well were measured at 450 nm to reflect the pre-protective and curative effects of ligand-modified AuCs against MPP$^+$ lesion.

Figure 20:
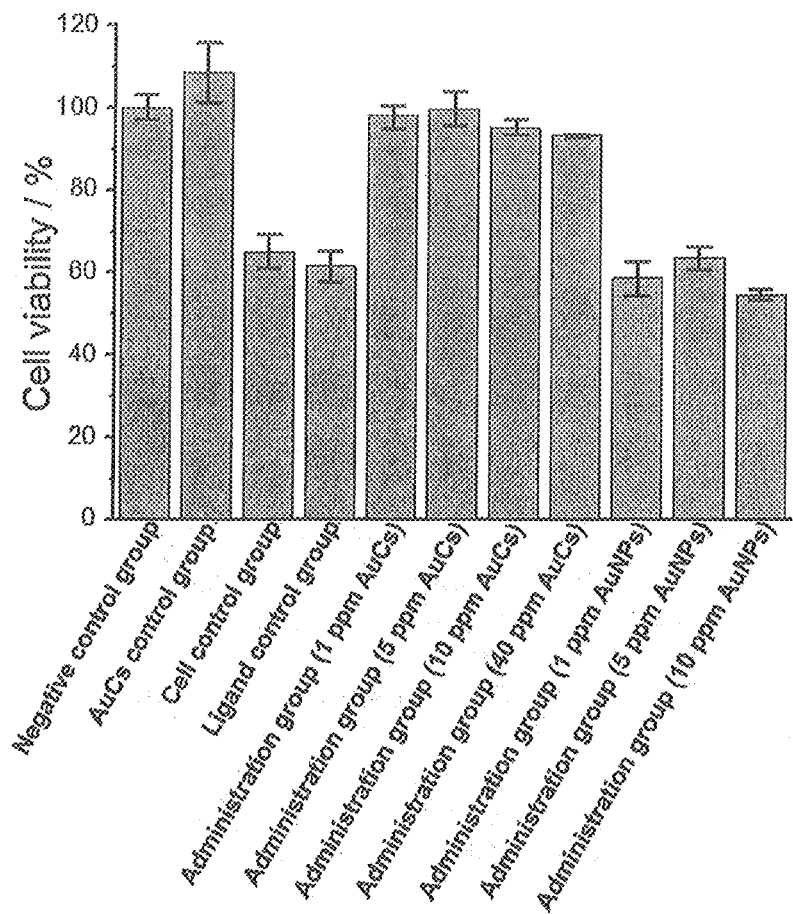
FIG. 20 shows diagrams showing the effect of an AuCs-containing substance on the cell viability of MPP$^+$-lesioned PD cell (SH-sy5y) model.

The experimental results of L-NIBC-modified AuCs or gold nanoparticles were taken for example, as shown in FIG. 20. The results indicated that after 24 hours of cultivation, the cell viability of the AuCs control group, adding 100 mM AuCs without MPP$^+$, increased to 108.5±7.1% relative to the blank control group (set as 100%) (P<0.01), suggesting that AuCs were nontoxic. The cell viability of the model control group, adding 1 mM MPP$^+$ but without AuCs, decreased to 65.1±4.0% (v.s. the blank control group, P<0.01), the cell viability of the ligand control group was 61.5±3.8% (v.s. the blank control group, P<0.01), suggesting that ligand only did not raise the viability of MPP$^+$ introduced cell model. While the cell viability of the administration group, adding 1 ppm, 5 ppm, 10 ppm and 40 ppm of AuCs respectively, increased to 97.9±2.8% (v.s. the model control group, P<0.01), 99.7±4.0% (v.s. the model control group, P<0.001), 95.3±1.7% (vs. the model control group, P<0.01) and 93.2±0.4% (v.s. the model control group, P<0.01) respectively, suggesting that the ligand-modified AuCs provided in the present invention had a protective effect on nerve cells in PD, and this effect was also originated from AuCs rather than the ligand. On the other hand, the corresponding gold nanoparticles with the same ligand did not help to improve the viability of the model cells at all experiment concentrations, indicating that the gold nanoparticles could not be used as a medicine for the prevention and treatment of PD.

The same steps were adopted to carry out the experiments for the AuCs modified with different ligands listed in Table 1. The effects were similar, so it will not be described in details here.

Embodiment 8: Experiment of MPP$^+$ Induced PD Cell (PC12) Model

The model of MPP$^+$ (100 mM) induced apoptosis of PC12 cells was used, combining with the flow cytometry technique to observe the protective effect of AuCs on MPP$^+$-induced cell injury and apoptosis in this experiment Specific method: A blank control group was the one without addition of MPP$^+$ and AuCs, an MPP$^+$ model group was the one with addition of MPP$^+$ only, an AuCs control group was the one with addition of AuCs only, and an experiment group was the one with addition of both MPP$^+$ and AuCs. In a experiment group, the solution of L-NIBC-modified AuCs with an average particle size of 1.8 nm was added into PC12 cell suspension (final concentration of AuCs was 20 ppm) half an hour later, MPP$^+$ was added, and the mixture was incubated for 24 hours, Annexin V-FITC/PI cell apoptosis detection kit (purchased from Roch) and FACSCalibur flow cytometer were used to detect the growth activity and apoptosis of the cells, and the data was acquired and analyzed by CellQuest Pro.

Figure 21:
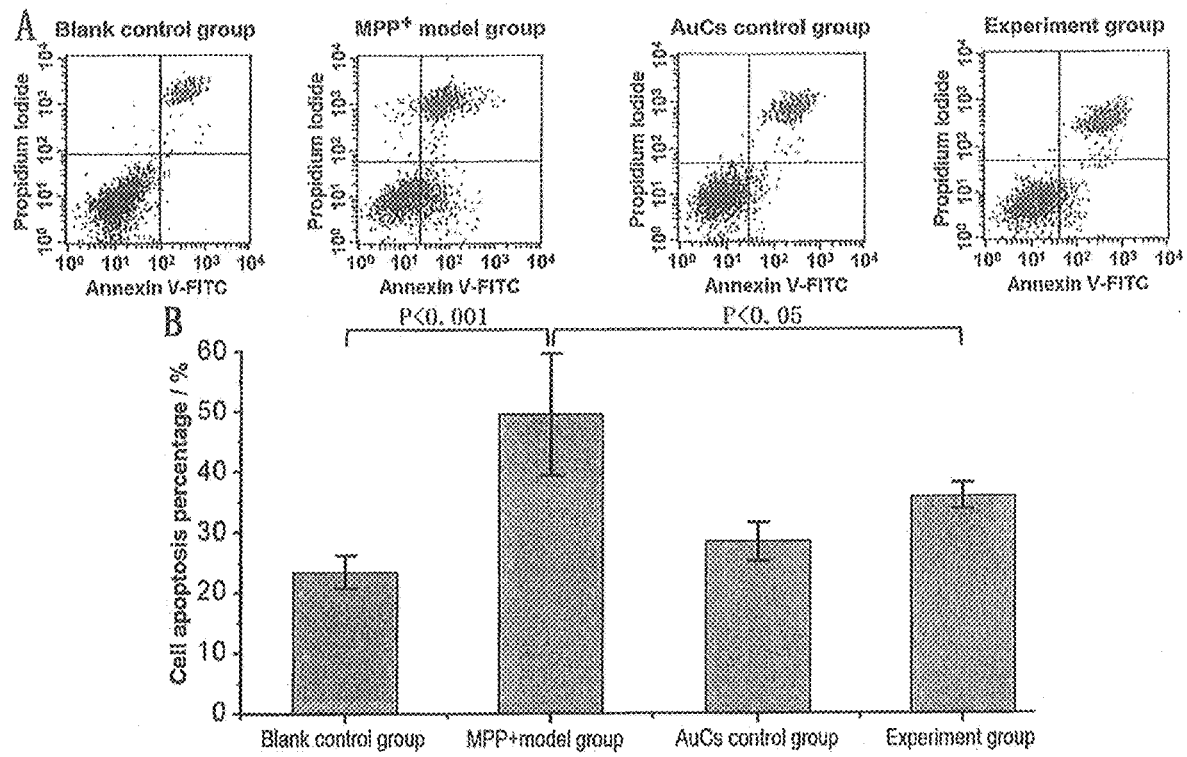
FIG. 21 shows diagrams showing the effect of an AuCs-containing substance on cell apoptosis of MPP$^+$-induced PD cell (PC12) model.

The experiment results were shown in FIG. 21. The cell cytometry detection results indicated that after incubation with MPP$^+$ for 24 h, as indicated in the cell cytometry detection, the cell apoptosis percentage of the blank control group, without addition of MPP$^+$, was 23.5±2.8%. When 20 ppm AuCs alone was coincubated with PC12 cells, the cell apoptosis percentage was 28.47±3.2%, which did not show a significant difference from the blank control group, suggesting that AuCs did not have apparent cytotoxic effect. The cell apoptosis percentage of the MPP$^+$ model group was 49.5±10.1%, which increased significantly compared with the blank control group (P<0.001). When PC12 cells were incubated with AuCs for a half hour before the addition of MPP$^+$, and were coincubated for 24 h, the cell apoptosis percentage decreased to 35.9±2.2%, compared with the MPP$^+$ model group, the cell apoptosis reduced significantly (P<0.05).

The same steps were adopted to carry out the experiments for the AuCs modified with different ligands listed in Table 1. The effects were similar, so it would not be described in details here.

The results of Embodiment 7 and Embodiment 8 jointly indicated that AuCs could efficiently improve the cell viability and significantly inhibit the cell apoptosis of MPP$^+$ induced PD cell model.

Embodiment 9: Experiment of MPTP Induced PD Mouse Model

Experiment 1

Experimental animals: 80 C57bl/6 male mice, 8 weeks old, body weight 25-30 g; 3 mice in each cage, were all raised in an environment of room temperature 22-27° C., 12 h circadian rhythms, with eating and drinking freely, and acclimated for 7 days.

MPTP induced PD mice model: Mice were randomly divided into four groups, 20 mice per group, including a blank control group, an AuCs normal control group, an MPTP model group and an AuCs treatment group. In the MPTP model group and the AuCs treatment group, 20 mg/kg (free base) MPTP was injected subcutaneously once every 2 h for four times. In the blank control group, 20 mg/kg normal saline was injected subcutaneously once every 2 h for four times. 8 h later than the last injection, in the blank control group and the MPTP model group, 10 µL normal saline was injected intravenously every day, while in the AuCs normal control group and the AuCs treatment group, 10 µL the normal saline solutions of ligand-modified AuCs listed in Table 1 (AuCs concentration 10 g/L) were intraperitoneally injected respectively every day. The injection lasted for 7 days. The animals were put in feeding boxes with clean padding, and water and food freely.

Behavioral test. Rotarod test, rotarod test requires animals to maintain balance and move continuously on a roller. It is a test widely used to test the motor coordination. Roller diameter is 6 cm and the rotation speed is 20 rpm. After the animals adapted to the roller for five times, the test was started at an interval of 1 min. The latency to fall off the rotarod was recorded consecutively for 5 times, and their average value was calculated.

Neurotransmitter determination: After behavioral test, the animals were sacrificed, and the mice striatum was taken and stored at −80° C. During measurement, the striatum was treated with 10 μL/mg (striatum) homogenate (0.1M perchloric acid, 0.1 mM EDTA-2Na), was cracked by ultrasonication in an ice bath for 30 min, was centrifuged in a refrigerated centrifuge at 10000 r/min for 10 min. The supernatant was taken and filtered with a 0.25 μm filter, was injected into the liquid chromatographic column of HPLC. The level of dopamine (DA) transmitter and its metabolites 3,4-dihydroxyphenylacetic acid (DOPAC) and homovanillic acid (HVA) in striatum were detected by the high performance liquid phase system in laboratory. The chromatographic column must be maintained with a freshly prepared mobile phase for 2 h before each test. HPLC conditions: flow rate: 1 mL/min; column temperature 30° C.; fluorescence detector excitation and absorption wavelengths were 280 nm and 330 nm respectively.

Determination of tyrosine hydroxylase: The brain tissues were taken out and fixed in 4 wt % PFA+2 wt % sucrose for 4-6 h, then were soaked in a 30 wt % sucrose solution, were embed with OCT after the tissues sinked to the bottom, were continuous coronal sectioned by frozen slicer, were stained in ABC (Avidibiotin-peroxidase complex) method, took out the frozen tissues of substantia nigra and sectioned them, were stained in TH and colored in diphenylamine, were observed under a microscope and taken photos.

The results indicated that the ligand-modified AuCs provided in the present invention could significantly improve the motor behaviors of MPTP induced PD model mice, increase the numbers of dopaminergic neurons, improve the intracerebral level of dopamine neurotransmitters. They could be used as substances containing AuCs to treat PD.

Experiment 2

Experimental animals: 80 C57bl/6 male mice, 8 weeks old, body weight 25-30 g; 3 mice in each cage, were all raised in an environment of room temperature 22-27° C., 12 h circadian rhythms, with eating and drinking freely, and acclimated for 7 days.

MPTP induced PD mice model: Mice were randomly divided into four groups, 20 mice per group, including a blank control group, AuCs control groups (based on the dose of AuCs, they were classified into low dose group and high dose group), an MPTP model group, AuCs treatment groups (based on the dose of AuCs, they were classified into low dose group and high dose group). In the MPTP model group and AuCs experiment groups, 30 mg/kg (free base) MPTP was injected intraperitoneally respectively once a day for 7 days consecutively. In the blank control group, 30 mg/kg normal saline was injected subcutaneously once a day for 7 days consecutively. In the low dose AuCs control group and the low dose AuCs treatment group, 100 μL normal saline solutions of 1 g/L L-NIBC-modified AuCs with an average particle size of 1.8 nm were injected intraperitoneally respectively once a day, while in the high dose AuCs control group and the high dose AuCs treatment group, 100 μL normal saline solutions of 4 g/L L-NIBC-modified AuCs with an average particle size of 1.8 nm were injected intraperitoneally respectively once a day, for 7 days consecutively. The animals were put in a feeding box with clean padding, and water and food freely.

1. Behavioral Testing:

(1) Spontaneous locomotor activity test: The animals were transferred from the cages to the autonomous activity detector. After the animals adapted to the new environment for 5 min, their spontaneous activities and the changes were recorded within 5 min. The activity distance and movement speed of the animals within 5 min were used to measure the activity of animals.

(2) Swim test: Refer to Donnan's test method (G. A. Donnan, G. L. Willis, S. J. Kaczmarezyk, P. Rowe, Journal of the Neurological Science 1987, 77, 185), the test mice were put into a Morris water tank. The depth of water was 60 cm and the temperature was 22° C. The swimming distance and swimming time of the animals within 10 min was recorded to measure the activity of the animals.

(3) Rotarod test: Rotorod test requires animals to maintain balance and move continuously on a roller. It is widely used to test the motor coordination. Roller diameter is 6 cm and the rotation speed is 20 rpm. After the animals adapted to the roller for five times, every test was performed with an interval of 1 min. The latency to fall off the rotarod was recorded. The test was conducted for 5 times consecutively and their average values were calculated.

2. Immunohistochemical detection in the striatum and the substantia nigra: After behavioral tests, 5 mice in each group were taken to conduct immunohistochemical detection in substantia nigra and striatum. After abdominal anesthesia by 1 mL 0.5% pentobarbital sodium, the chests were opened, 15 mL of 0.9% normal saline was used to rinse the blood from aorta at first, and then 100 mL 0.1 mol/L of phosphate buffer solution (PBS, pH 7.2) containing 4% paraformaldehyde was used for perfusion (first fast then slowly) and fixation for 1 h. The brains were taken out after perfusion and fixation, were put into 4% paraformaldehyde, were embed with paraffin in reference to mice brain map, substantia nigra and striatum were coronal sectioned. The thickness of brain slices was 3 μm/section. The obtained brain slices were used in immunofluorescence, hypersensitive two-step immunohistochemistry and other experiments. immunohistochemical staining steps were as follows: The obtained brain slices were in 0.3% $H_2O_2$ methanol solution (30% $H_2O_2$ 1 mL+methanol 80 mL+PBS 19 mL) for 30 min, in 0.3% Triton X-100 PBS for 30 min, were soaked into mice anti-tyrosine hydroxylase (TH) monoclonal antibody (1:200) or IBa1 (dilution ratio 1:250) and incubated for 48 h (4° C.), were soaked into biotinylated rabbit anti-mouse secondary antibody (1:500) and incubated for 2 h (room temperature). They were rapidly rinsed with distilled water and colored by nickel ammonium sulfate enhanced DAB blue reaction method for 20~30 min. When the positive product was dark blue and the background was clear, the brain slices were rinsed with distilled water for 3 times to stop coloration. After each of the above steps, the brain slices should be rinsed by 0.01 mol/L PBS for three times and for 10 min each time. And the primary antibody used here was diluted with PBS containing 1% bovine serum and 0.3% Triton X-100, and the complex of secondary antibody and ABC were diluted with PBS. Adherence of brain slices, dehydration and sealing with transparent neutral gum were conducted.

3. Protein immunoblotting (WB) assay: Tyrosine hydroxylase (TH) is a key enzyme in the biosynthetic pathway of dopamine (DA), and immunohistochemistry of TH can show changes in DA-ergic neurons in substantia nigra and striatum (D. Luo, J. Zhao, Y Cheng, S. M. Lee, J. Rong, Molecular Neurobiology 2017, DOI: 10.1007/s12035-017-0486-6). After behavioral tests, five mice were taken from each group to conduct striatum WB detection, the needed brain tissues were take out on ice, were cracked in RIPA lysate, were centrifuged at 4° C. and 12000 g for 30 min to homogenate, proteins were extracted to prepare samples, SDS-polyacrylamide gel electrophoresis at 55V-

60V for 4.5 h, and the proteins were transferred to the membrane by semi-dry method at constant current of 60 mA for about 1.5 h. The membrane was blocked with 5% skimmed milk at room temperature for 1 h; TBST-diluted rabbit TH antibody (dilution ratio 1:300) was added, stayed overnight at 4° C.; the antibody was recovered, the membrane was washed with TBST for three times, 10 min each time; TBST-diluted IRDye R 680RD Goat anti-Rabbit (dilution ratio 1:3000) was added; the membrane was washed with TBST for three times, 10 min each time; protein signals were scanned by dual-color infrared laser imaging system.

Figure 22:
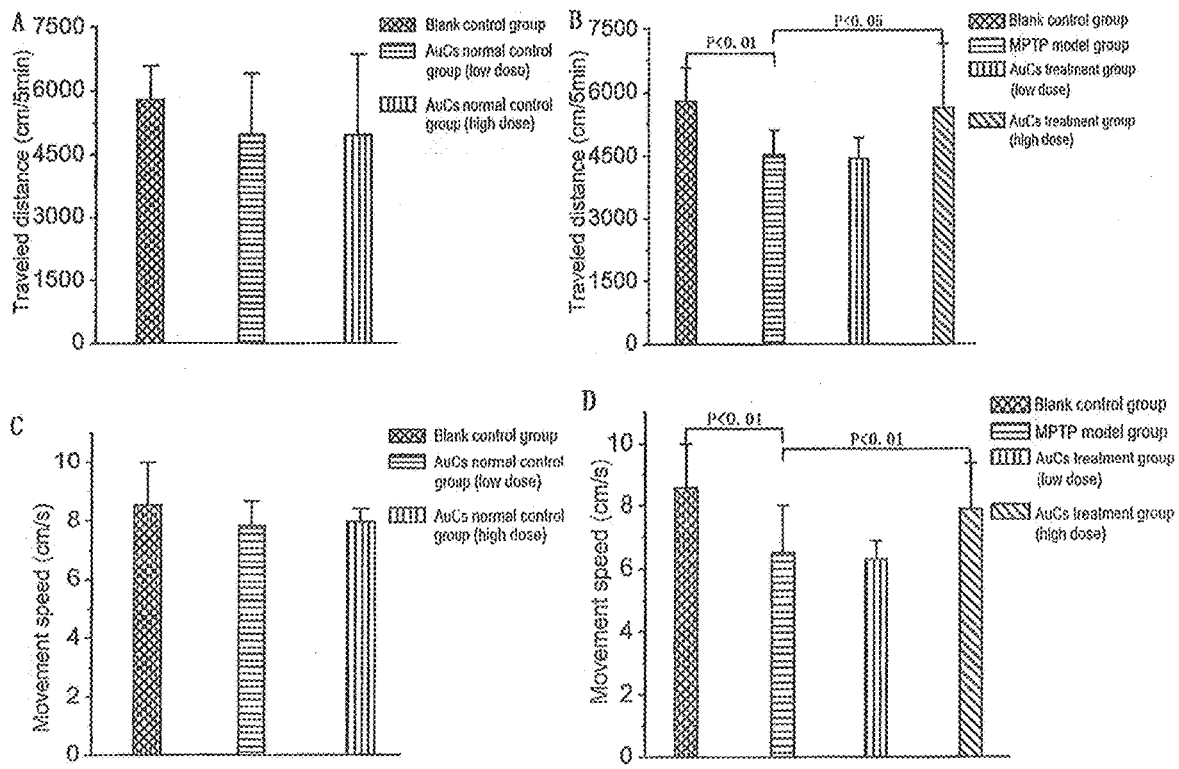
FIG. 22 shows diagrams showing the effect of an AuCs-containing substance on the locomotor activity of MPTP-lesioned model mice.

The test results of the spontaneous locomotor activity of mice were shown in FIG. 22. Three to five minutes after administration of MPTP, mice showed tremor, decreased movement, arched back, hind limb opening, gait instability, vertical tail, and vertical hair. Individual epileptic seizures occurred after about 30 to 60 minutes. The above symptoms gradually reduced, and the mice returned to normal after 24 hours. However, with the increase of the number of administrations, the acute response was relieved, but after 24 hours, the performance of exercise decreased, gait instability and slow response became more obvious. After continuous administration of MPTP for seven days, the spontaneous activity distance and movement speed of the mice were significantly lower than those of the blank control group (P<0.01), showing the symptoms of bradykinesia. The administration of AuCs alone had no significant effect on the spontaneous activity distance and movement speed of normal mice (panels A and C of FIG. 22). The combined administration of AuCs (high dose) in mice of the MPTP model could significantly increase the spontaneous activity distance and movement speed of the mice (panels B and D of FIG. 22), suggesting that AuCs played a significant role in improving the spontaneous locomotor activity of MPTP model mice. Compared with MPTP model group, the difference was significant (spontaneous activity distance: P<0.05; movement speed: P<0.01).

Figure 23:
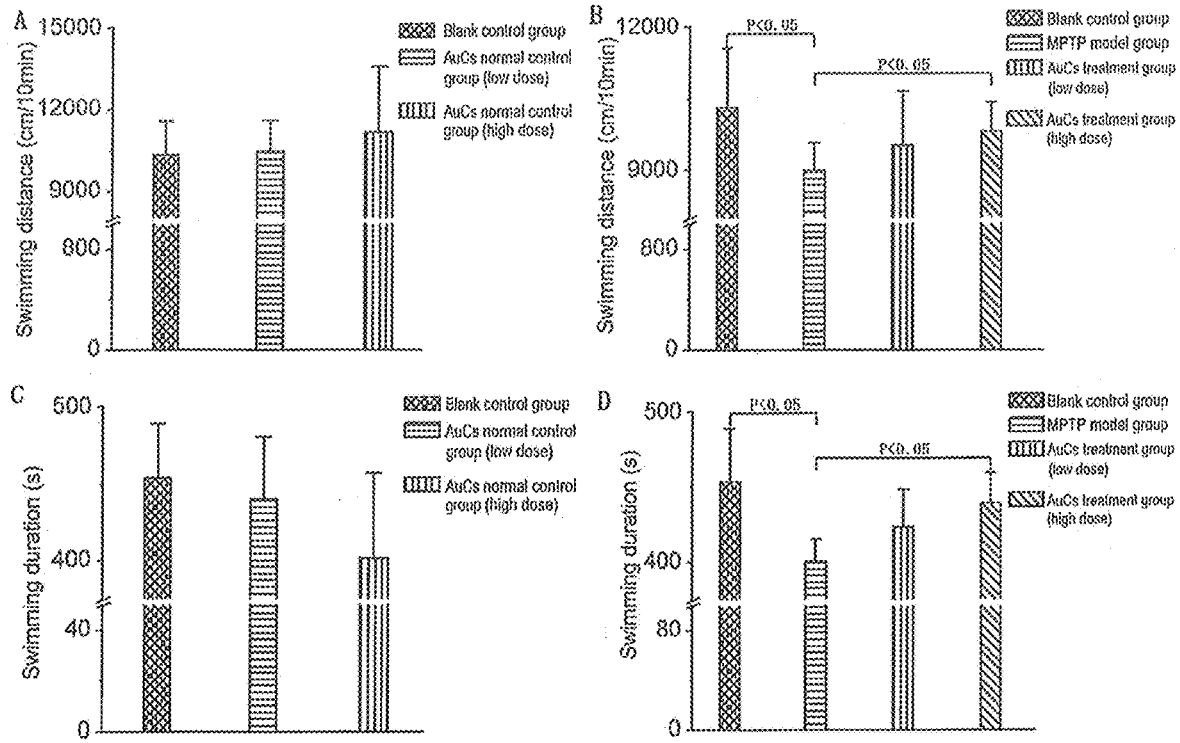
FIG. 23 shows diagrams showing the effect of an AuCs-containing substance on the swimming ability of the MPTP-lesioned model mice.

The results of the swim test of mice were shown in FIG. 23. After seven days of continuous MPTP injection, the mice were placed in a water tank to do the swimming test Longer swimming time and farther swimming distance of mice indicate the mice had better motor coordination of limbs. The blank control group and the AuCs control group didn't have significant effect on the swimming time and swimming distance of mice (panels A and C of FIG. 23). Compared with the blank control group, MPTP model group showed significant decrease of swimming distance in 10 min (P<0.05), and significant decrease of the swimming time in the water tank (P<0.05), suggesting that MPTP significantly reduced the motor ability of swimming for the mice. Compared with the MPTP model group, the AuCs treatment group with administration of AuCs (high dose) and MPTP showed increase of swimming distance (P<0.05) and significant increase of swimming time (P<0.05) (panels B and D of FIG. 23), suggesting that AuCs significantly improved MPTP-induced motor behavior disorder of swimming for the mice.

Figure 24:
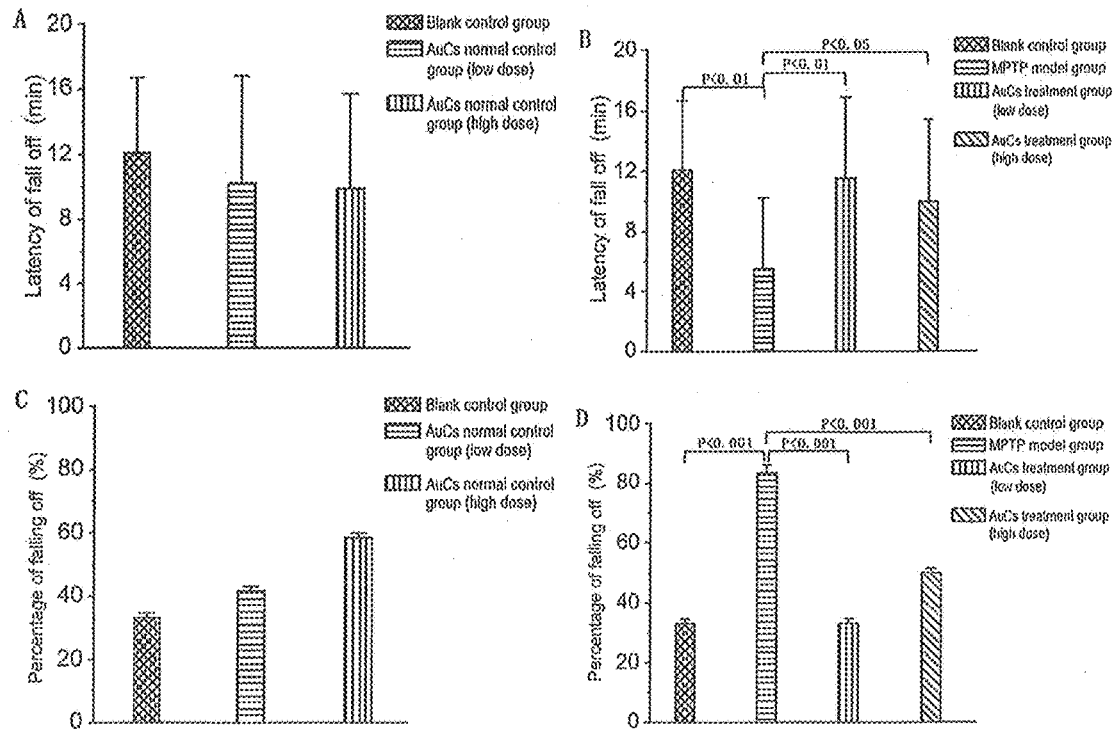
FIG. 24 shows diagrams showing the effect of an AuCs-containing substance on the rotarod behavior of the MPTP-lesioned model mice.

The results of the mouse rotarod test were shown in FIG. 24. After the mice were injected with MPTP consecutively for 7 days, they were subjected to the rotarod test. In the blank control group administrated with normal saline, the latency to fall off the rotarod and the percentage of mice falling off the rotarod were 12.1±4.6 min and 33.3±1.5% (panels A and C of FIG. 24). Compared with the blank control group, the rod drop latency of the mice in the MPTP model group was shortened significantly to 5.5±3.7 min, and the rod drop percentage increased significantly to 83.3±3.4%. It was indicated that after the administration of MPTP, the motor coordination of mice decreased and the mice, could not grasp the rod stably and were liable to falling off the rotarod (panels B and D of FIG. 24). The administration of AuCs alone had no significant effect on the fall latency of mice (image A of FIG. 24), but during long-time roller motion, the percentage of mice falling off the rotarod increased significantly (P<0.001 v.s. the blank control group). It was indicated that the self-administration of AuCs had a certain effect on the roller behavior of mice (panel C of FIG. 24). But compared with the MPTP model group, the AuCs treatment group with administration of both MFTP and AuCs showed obvious increase of latency to fall off the rotarod (low dose group: P<0.01; high dose group: P<0.05), and significant decrease of the percentage falling off the rotarod (P<0.001 for both the high dose group and the low dose group). The results were shown in panels B and D of FIG. 24. This indicated that AuCs have the effect to improve MPTP-induced motor coordination dysfunction.

Figure 25:
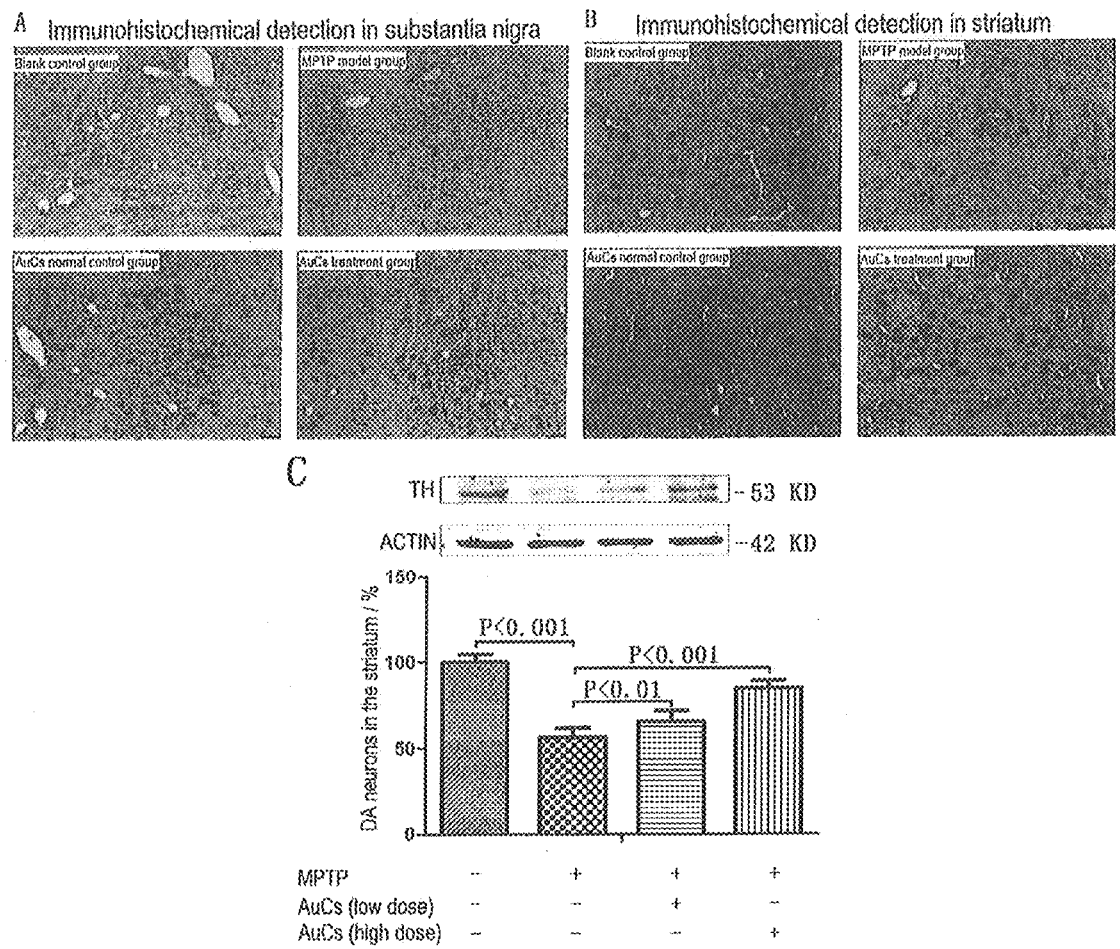
FIG. 25 shows diagrams showing the effect of an AuCs-containing substance on DA-ergic neurons in substantia nigra and striatum of the MPTP-lesioned model mice.

The results of immunohistochemical detection in substantia nigra and striatum and WB detection of striatum were shown in FIG. 25. Compared with the blank control group, the MPTP model group showed obvious decrease in the number of TH immunopositive neurons (i.e., DA-ergic neurons) in substantia nigra with shrinkage of residual neurons and reduction or disappearance of neurites, and reduction of TH immunopositive neurons in striatum and decrease of nerve fiber density. The results of WB analysis indicated that DA-ergic neurons in striatum reduced to 55.8±5.6% (blank control group: 100%) (v.s. the blank control group, P<0.01, see panel C of FIG. 25). The administration of AuCs alone didn't have significant effect on TH immunopositive neurons and the density of nerve fibers in substantia nigra and striatum (panels A and B of FIG. 25). The combined administration of AuCs and MPTP could significantly inhibit MPTP induced down-regulation of TH immunopositive expression in cells and neurofilaments of substantia nigra and striatum. The results of WB analysis indicated that when low dose AuCs were adopted, the ratio of DA-ergic neurons in striatum was 65.6±6.3% of the blank control group (P<0.01, v.s. the MPTP model group, see panel C of FIG. 25), and when high dose AuCs were adopted, the ratio of DA-ergic neurons in striatum reached 84.7±4.5% of the blank control group (P<0.001, v.s. the MPTP model group). The results indicate that AuCs had a significant effect on resisting MFTP cytotoxicity, and showed a remarkable protective effect against DA-ergic neuron loss in substantia nigra and striatum.

The same method was also adopted to conduct experiments using the AuCs modified with different ligands listed in Table 1. The effects were similar, so it would not be described in details here.

The above results indicated that the ligand-modified AuCs provided in the present invention could significantly improve the spontaneous locomotor activity, motor ability and body coordination ability of MPTP induced PD model mice, and had a significant protective effect against DA-ergic neuron loss in substantia nigra and striatum, indicating that substances containing AuCs can be used to treat PD.

Embodiment 10: Biosafety Evaluation

1. SH-sy5y cell line was adopted to evaluate the biosafety of the substances containing AuCs at the cell level.

Specific method: SH-sy5y cells in the logarithmic growth phase of cells (cells at passage 6) were collected. The concentration of cell suspension was adjusted, and added 100 μL into each well. The cells were plated, and the cell density was adjusted to 1000-10000 per well. The cell cuture plates (the marginal wells of 96-well plates were filled with cell culture medium) were put in a cell incubator and incubated in a 5% $CO_2$, 37° C. environment for 24 h so that the cells attached to the wall. The 96-well plates were taken out, and then put in a biosafety cabinet after disinfection by alcohol. The original cell culture medium was sucked out, and then solutions of ligand-modified AuCs listed in Table 1 were added, which were diluted with cell culture medium to obtain a final concentration of 1 ppm, 10 ppm, 50 ppm, 100 ppm, 200 ppm and 500 ppm, respectively. An equal volume of fresh cell culture medium was added to the control group (no AuCs). And put it in a cell incubator, and incubated for 48 h. 6 duplicate wells were set for each of the experiment group and the control group. After 48 h of incubation, the culture medium was removed by centrifuging, then washed with PBS for 2-3 times. 100 μL fresh culture medium and 20 μL methyl thiazolyl tetrazolium (MTT) solution (5 mg/ml, i.e., 0.5% MTT) were added to each well, and continued to be cultivated for 4 h. The cultivation was terminated, the 96-well plate was taken out, and centrifuged (1000 r/min) for 10 min. The supernatant was sucked out, and 200 μL DMSO was added to each well, and put on a shaking table, and oscillated at a low speed for 10 min till the color in the wells was uniform and crystal was fully dissolved. The absorbance of each well was measured at 490 nm by microplate reader. The above operations must be conducted in a sterile environment Except detection, all the steps were completed in a biosafety cabinet. The experimental supplies must be disinfected in an autoclave before use.

Figure 26:
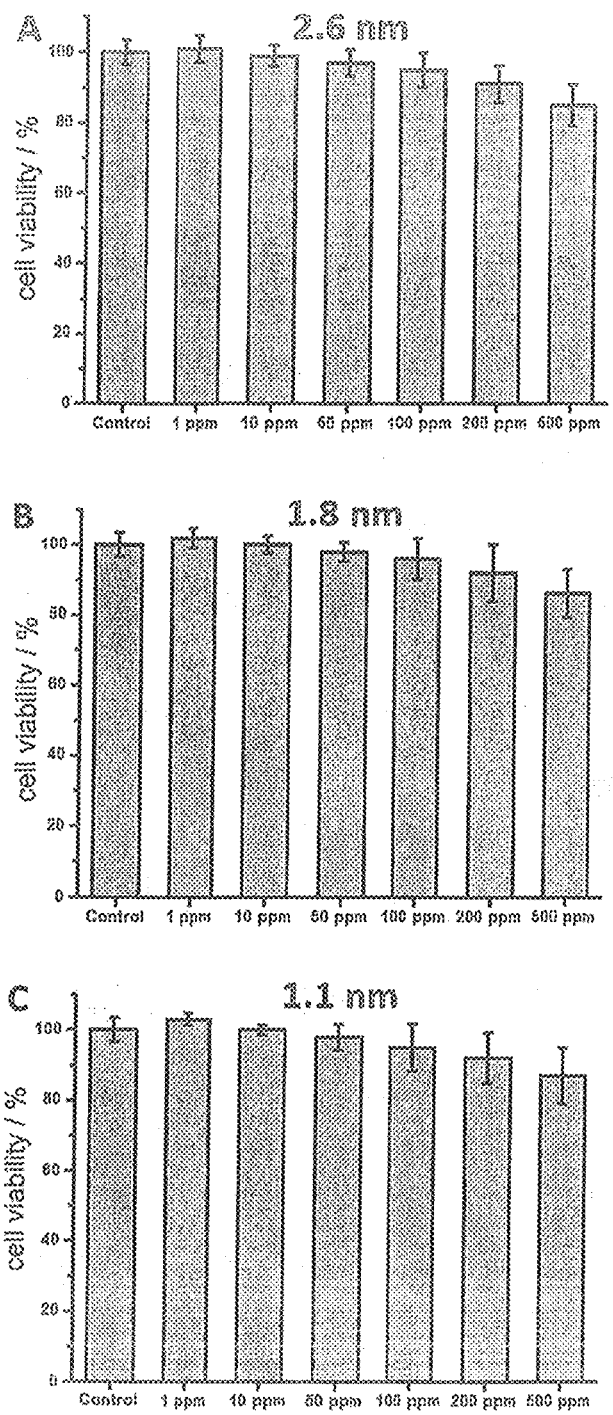
FIG. 26 shows diagrams showing the effect of an AuCs-containing substance of different particle sizes and different concentrations on SH-sy5y neuroblastoma cell viability.

L-NIBC-modified AuCs in Embodiment 2 were taken for example, the results were shown in FIG. 26 where panels A-C showed the effects of AuCs with particle sizes of 2.6 nm, 1.8 nm or 1.1 nm and at final concentrations of 1 ppm, 10 ppm, 50 ppm, 100 ppm, 200 ppm or 500 ppm on SH-sy5y cell viability. It was indicated that at a fairly high concentration (such as: 100 ppm), the addition of L-NIBC-modified AuCs almost didn't have any influence on cell viability. At a higher concentration (such as: 200 and 500 ppm), the addition of L-NIBC-modified AuCs would cause slight cell injury (cell death rate is less than 20%). Since 100 ppm was much higher than the lowest effect concentration of the AuCs (0.1~1 ppm or lower), it could be concluded that L-NIBC-modified AuCs had high safety at the cell level.

Other ligand-modified AuCs with different sizes listed in Table 1 also had similar effects. They would not be described in detail here.

2. Adopt mouse acute toxicity study to evaluate the acute toxicity of substances containing AuCs.

Specific method: For different ligand-modified AuCs listed in Table 1 (L-NIBC-modified AuCs with an average diameter of 1.8 nm in Embodiment 2 was taken for example), 60 adult mice were taken, and divided into four groups with 15 mice in each group, which were: a control group and three experiment groups. In the control group, mice were fed normally, while in the three experiment groups, mice were fed with AuCs by oral administration (by gavage) at a dose of 0.1 g/Kg body weight, 0.3 g/Kg body weight and 1 g/Kg body weight a day respectively for one week under the condition of normal diet. The mice were fed normally for 30 days after the feeding of AuCs was finished. Abnormal responses of the mice were observed.

In the mice experiment, the ingestion of AuCs with different sizes at three concentrations had no influence on the survival and activity of mice. Even though for high dose intake of 1 g/Kg body weight, the mice still remained healthy.

Other ligand-modified AuCs listed in Table 1 also had similar results. They would not be described in details here. Based on the above results, it could be concluded that AuCs were very safe.

Embodiment 11: Tissue Distribution and Metabolic Distribution of the CuCs-Containing Substances in Mice Experiment 1

Operating steps: 80 mice were randomly divided into four groups, 20 mice in each group, and fed with ligand-modified AuCs listed in Table 1 by oral administration (by gavage) at doses of 100 mg/kg, 20 mg/kg, 5 mg/Kg and 1 mg/kg respectively in the groups. After feeding of AuCs, the 20 mice in each group were randomly divided into 4 subgroups with 5 mice in each subgroup. They were sacrificed at the time points of 2 h, 6 h, 24 h and 48 h respectively after feeding. Heart, liver, spleen, lung, kidney and brain tissues were taken separately. Each tissue was weighed, and 2 mL water was added to homogenize, and then 2 mL aqua regia was added and mixed under vortex, and oscillated for 72 h on an oscillator. 2 wt % nitric acid solution was added to a final volume of 10 mL, and centrifuged at 15000 rpm for 15 min. 4 mL of supernatant was sucked, and the content of gold element in the tissue fluid was measured by atomic absorption spectrometry.

The results indicated that AuCs could pass through the blood-brain barrier and reached the brain. They could be excreted out of the body over time, so they didn't have obvious accumulation in the body. Therefore, the substances containing AuCs provided in the present invention had a good prospect in the application of preparation of medication treating AD or PD.

Experiment 2

Operating steps: 80 mice were randomly divided into four groups with 20 mice in each group, and injected intraperitoneally with ligand-modified AuCs listed in Table 1. The doses of AuCs (L-NIBC-modified AuCs with an average diameter of 1.8 nm were taken for example) in each group were 100 ppm, 20 mg ppm, 5 ppm and 1 ppm of mouse body weight respectively. After injection of AuCs, the 20 mice in each group were randomly divided into 4 groups, 5 mice in each group. They were sacrificed at time points of 2 h, 6 h, 24 h and 48 h respectively after feeding. Heart, liver, spleen, lung, kidney and brain tissues were taken separately. Each tissue was weigh, and 2 mL water was added to homogenize, then 2 mL aqua regia was added and mixed under vortex, and oscillated for 72 h on an oscillator 2 wt % nitric acid solution was added to a final volume of 5 mL, and centrifuged at 15000 rpm for 15 min. 1 mL supernatant was sucked, and the content of gold element in the tissue fluid was measured by atomic absorption spectrometry.

Above steps were adopted to carry out experiments for AuCs modified with other ligands listed in Table 1.

The results indicated that after 2 h, the content of gold element in the brain reached 1%-10% of initial concentration. After 6 h, the content in the brain could be maintained at a similar level. After 24 h, the content in the brain decreased significantly. At hour 48 h, the content decreased to near or below the detection limit except for the specimens at a dose of 100 ppm. The above results indicated that substances containing AuCs also had good biosafety at the animal level, which can pass through the blood-brain barrier, and had no obvious accumulation in the body.

In summary, the above experiment results illustrated the following points (the "gold nanoparticles" and "AuCs" mentioned below all refer to the cases with ligand modification):

(1) In the experiment (Embodiment 3) for Aβ aggregation in vitro, it was found that the effect of gold nanoparticles on Aβ aggregation kinetics was related to size. When the particle diameter was greater than or equal to 10.1 nm, the addition of gold nanoparticles could accelerate the aggregation of Aβ, and when the particle size was smaller than or equal to 6.0 nm, the aggregation of Aβ was inhibited, but complete inhibition of AB aggregation could not be achieved. However, when AuCs were used (average diameter is less than 3 nm), all the AuCs could significantly inhibit Aβ aggregation in vitro, and this effect was related to the concentration of AuCs. When the concentration of AuCs reached 5-10 ppm, the aggregation of Aβ could be inhibited completely, and the minimum concentration required for complete inhibition was related to the type of ligand and the diameter of AuCs. In the in vitro experiment (Embodiment 6) for inhibition of α-syn aggregation, it was also found that AuCs had the same effect of complete inhibition of α-syn aggregation and fibrosis.

(2) In Aβ induced cell AD model and MPP$^+$ induced cell PD model experiment (Embodiment 4, Embodiment 7 and Embodiment 8), it was found that gold nanoparticles with small particle sizes (for example, gold nanoparticles with an average diameter of 3.6 nm or 6.0 nm) didn't have a significant effect on the improvement of cell viability of Aβ induced cell AD model and MPP$^+$ induced cell PD model, suggesting that gold nanoparticles didn't show obvious medicinal efficacy on AD and PD at the cell level, so they could not be directly used as active ingredient to prepare medication treating AD or PD. However, for different ligand-modified AuCs with different sizes used in the present invention (the average diameter was less than 3 nm), it was found that a very low dose of AuCs (such as: 0.1-1 ppm) could still raise the cell viability of the two models from 50%-65% to above 95%. It indicated that at the cell level, the medicinal efficacy of AuCs was significant. As the ligands had no effect on Aβ aggregation and both the two cell models (Embodiments 4, 7 and 8), it could be concluded that the medicinal efficacy of AuCs was from AuCs themselves. This offered a new approach for the application of AuCs.

(3) Further, the transgenic AD mice model and the MPTP induced PD mice model (Embodiment 5 and Embodiment 9) were used in the present invention to further verify the medicinal efficacy of AuCs, indicating that the AuCs played a significant role in improving mouse's cognitive behavioral ability and motor behavioral ability, inhibiting the formation of senile plaques in the brain and inhibiting the specific apoptosis of DA-ergic neurons induced by MPTP in substantia nigra and striatal, and could be used as preventive or therapeutic medication for related diseases.

(4) In the experiment for further evaluation of biosafety (Embodiment 10), when AuCs at a concentration of 100 ppm (by weight) were co-cultured with nerve cells, they didn't have an obvious influence on the viability of cells; when the concentration exceeded 100 ppm (much higher than the lowest effect concentration of the AuCs), the cell viability decreased slightly. As the lowest effect concentration of AuCs (0.1-1 ppm) was much lower than 100 ppm, it could be concluded that AuCs had excellent biosafety at the cell level. In the mouse acute toxicity test, it had been found that a dose of 1 g/Kg body weight (equivalent to 1000 ppm) AuCs administered once a day for seven days consecutively did not cause adverse effect. In the study of in vivo distribution and pharmacokinetics in mice (Embodiment 11), the content of gold element in the brain reached 1%-10% of the initial concentration after 2 h. After 6 h, the content in the brain maintained at a similar level. After 24 h, the content in the brain decreased significantly. At 48 h, the content decreased to below the detection limit except for the specimens at a dose of 100 ppm. The above results indicate that a substance containing AuCs also has good biosafety at the animal level, could pass through the blood-brain barrier, and has no obvious accumulation in the body, so it had a good prospect in the application in preparation of medication treating AD or PD.

(5) Compared with current technology, the ligands used in the present invention were not specifically designed for the aggregation behaviors of Aβ and α-syn, and the contrast experiment indicated that the ligands used had no obvious effect on the aggregation of Aβ and α-syn (Embodiment 3). But since the size of AuCs was smaller than the size of the protein itself, the aggregation of A and α-syn could be greatly inhibited by the combination of the size effect and the weak molecular interactions. The excellent efficacies in Aβ induced AD cell model and transgenic animal model further confirmed the feasibility of substances containing AuCs in the preparation of medication for the treatment of AD. In addition, the excellent efficacies of substances containing AuCs in MPP$^+$ induced PD cell model and MPTP induced PD animal model indicated that substances containing AuCs also had broad application prospects in the preparation of medication treating other neurodegenerative diseases. Moreover, since MPP$^+$ induced PD cell model and the MPTP induced PD animal model didn't involve protein fibrosis, but acted on deeper mechanisms including function of signal transduction related to energy metabolism and neurotransmitter metabolism of nerve cells, it could be speculated that substances containing AuCs could not only affect protein fibrosis but also influence the process of neurodegenerative diseases at a deeper level. It will be of great significance to the research and development of new medication for neurodegenerative diseases.

INDUSTRIAL APPLICABILITY

The substances containing AuCs provided in the present invention can improve mouse's cognitive behavior and motor behavior abilities and inhibit the formation of senile plaques in the brain in AD transgenic mouse model and MPTP induced PD mouse model, and have good biosafety at the animal level. They are suitable for industrial applications.

What is claimed is:

1. A method for treating a subject with Parkinson's disease, said method comprising:
   administrating a pharmaceutical composition into the subject with Parkinson's disease in an effective amount;
   wherein said pharmaceutical composition comprising a substance containing gold clusters (AuCs); wherein said substance comprises:
   AuCs; and
   a ligand Y coating the AuCs externally, herein the ligand Y is a thiol-containing compound;

wherein the AuCs have a gold core diameter smaller than 3 nm;
wherein the thiol-containing compound is one selected from the group consisting of:
N-isobutyryl-L-cysteine (L-NIBC) and N-isobutyryl-D-cysteine (D-NIBC).

2. The method of claim 1, wherein the AuCs have a gold core diameter in the range of 0.5-2.6 nm.

* * * * *